United States Patent
Numasawa et al.

(10) Patent No.: US 11,474,341 B2
(45) Date of Patent: Oct. 18, 2022

(54) ELECTRONIC COMPONENT UNIT

(71) Applicant: Fujikura Ltd., Tokyo (JP)

(72) Inventors: Yoshinobu Numasawa, Sakura (JP); Masahiro Kondo, Sakura (JP); Daisuke Murakami, Sakura (JP); Issei Miyake, Tokyo (JP); Masayuki Suzuki, Tokyo (JP)

(73) Assignee: Fujikura Ltd., Tokyo (JP)

(*) Notice: Subject to any disclaimer, the term of this patent is extended or adjusted under 35 U.S.C. 154(b) by 69 days.

(21) Appl. No.: 17/267,207

(22) PCT Filed: Aug. 30, 2019

(86) PCT No.: PCT/JP2019/034069
§ 371 (c)(1),
(2) Date: Feb. 9, 2021

(87) PCT Pub. No.: WO2020/050158
PCT Pub. Date: Mar. 12, 2020

(65) Prior Publication Data
US 2021/0311297 A1  Oct. 7, 2021

(30) Foreign Application Priority Data

Sep. 6, 2018 (JP) .............................. JP2018-167119

(51) Int. Cl.
G02B 23/24 (2006.01)
H04N 5/225 (2006.01)
H04N 5/335 (2011.01)

(52) U.S. Cl.
CPC ....... G02B 23/2484 (2013.01); H04N 5/2252 (2013.01); H04N 5/335 (2013.01); *H04N 2005/2255* (2013.01)

(58) Field of Classification Search
CPC .. G02B 23/2484; H04N 5/2252; H04N 5/335; H04N 2005/2255; A61B 1/00114; H01R 12/52
See application file for complete search history.

(56) References Cited

U.S. PATENT DOCUMENTS 5,281,771 A * 1/1994 Swift ..................... H05K 3/368
174/262
6,531,662 B1 * 3/2003 Nakamura ............ H01R 12/52
361/776

(Continued)

FOREIGN PATENT DOCUMENTS

JP S56-123381 U 9/1981
JP 2006-109097 A 4/2006

(Continued)

OTHER PUBLICATIONS

English translation of the International Search Report issued in International Application No. PCT/JP2019/034069, dated Oct. 8, 2019 (2 pages).

*Primary Examiner* — Jefferey F Harold
*Assistant Examiner* — Timothy R Newlin
(74) *Attorney, Agent, or Firm* — Osha Bergman Watanabe & Burton LLP

(57) ABSTRACT

An electronic component unit includes: an electronic module in which a rear substrate is electrically connected via an electric cable to an electronic element; an external connection terminal that is electrically connected to an external circuit; a relay substrate including a terminal connection electrode to which the external connection terminal is electrically connected either directly or via a connection conductor; and a relay connector on the relay substrate. The electronic element is any one of: an imaging element; a laser element; and a sensor element.

5 Claims, 14 Drawing Sheets

(56) References Cited

U.S. PATENT DOCUMENTS

| | | | | |
|---|---|---|---|---|
| 9,667,843 | B2* | 5/2017 | Wada | H04N 5/2253 |
| 2001/0023143 | A1* | 9/2001 | Middlehurst | H01R 12/716 |
| | | | | 439/79 |
| 2009/0163052 | A1* | 6/2009 | Zhu | H01R 12/52 |
| | | | | 439/74 |
| 2009/0268019 | A1* | 10/2009 | Ishii | G03B 17/02 |
| | | | | 348/294 |
| 2010/0231702 | A1* | 9/2010 | Tsujimura | A61B 1/00124 |
| | | | | 348/E7.091 |
| 2012/0104230 | A1* | 5/2012 | Eismann | A61B 1/051 |
| | | | | 438/66 |
| 2015/0078818 | A1* | 3/2015 | Chitaka | H05K 7/14 |
| | | | | 403/373 |
| 2017/0035279 | A1* | 2/2017 | Fujii | A61B 1/051 |
| 2017/0071453 | A1* | 3/2017 | Mikami | A61B 1/00096 |
| 2017/0123200 | A1* | 5/2017 | Suyama | A61B 1/0011 |
| 2017/0224203 | A1* | 8/2017 | Tanahashi | H05K 3/366 |
| 2018/0049627 | A1* | 2/2018 | Adachi | G03B 17/02 |
| 2018/0070803 | A1* | 3/2018 | Mikami | A61B 1/00117 |
| 2018/0211989 | A1* | 7/2018 | Hogyoku | H01L 24/17 |
| 2020/0054202 | A1* | 2/2020 | Yamamoto | A61B 1/0011 |

FOREIGN PATENT DOCUMENTS

| | | |
|---|---|---|
| JP | 2009-135353 A | 6/2009 |
| JP | 2013-229437 A | 11/2013 |
| JP | 2016-022005 A | 2/2016 |
| WO | 2016/143179 A1 | 9/2016 |

\* cited by examiner

ELECTRONIC COMPONENT UNIT

CROSS-REFERENCE TO RELATED APPLICATIONS

Priority is claimed on Japanese Patent Application No. 2018-167119 filed on Sep. 6, 2018, the content of which is incorporated herein by reference.

TECHNICAL FIELD

The present invention relates to an electronic component unit.

BACKGROUND

In electronic endoscopes, a number of imaging modules having a configuration in which a solid-state imaging element (hereinafter, also simply referred to as an imaging element) is electrically connected to a tip of an electric cable via a wiring substrate are adopted (for example, Patent Document 1).

In this type of imaging module, the tips of a plurality of the electric cables are electrically connected to the wiring lines of the wiring substrate, and each electric cable is electrically connected to the imaging element by the wiring line of the wiring substrate.

Additionally, regarding this type of imaging module, a step of passing the imaging module through a thin resin tube is performed when the imaging module is incorporated into a videoscope device of an electronic endoscope system. After this step, soldering an end (rear end) opposite to the tip of each electric cable to a relay substrate electrically connected to a video processing display device including a monitor has been widely performed.

PATENT LITERATURE

Patent Document 1: Japanese Unexamined Patent Application, First Publication No. 2006-109097

In the step of passing the imaging module through the resin tube, in addition to a case where the imaging module is inserted into the tube from the imaging element side, the imaging module is inserted into the tube from a rear end (a proximal end, specifically, a rear end of the electric cable) thereof has also been widely used.

For example, in a case where an electrical connection plug, which is attachably and detachably fitted to the receptacle on the video processing display device side is assembled to the rear end of the imaging module, it is difficult to insert the imaging module through the tube from the rear end side thereof. For this reason, in the step of passing the imaging module through the tube from the rear end thereof, the rear end of the electric cable of the imaging module is inserted into the tube with the cable end without a plug. Since no electrical connection plug is placed at the cable end, as a result, it is necessary to solder the end part of the cable to the substrate (relay substrate) when the videoscope device is assembled or repaired, and substantial time and effort are taken for this work. Additionally, in a case where an ultra-fine cable is used, the degree of difficulty of the soldering work is high and the soldering time and effort are increased.

SUMMARY

The present invention provides an electronic component unit that can simply and easily perform an electrical connection between an electronic module such as an imaging module and other devices without using a receptacle and a plug inserted and fitted into the receptacle.

An electronic component unit according to one or more embodiments of the present invention includes an electronic module in which a rear substrate is electrically connected to an electronic element of any one of an imaging element, a laser element, and a sensor element via an electric cable; an external connection terminal that is electrically connected to an external circuit; a relay substrate including a terminal connection electrode to which the external connection terminal is electrically connected directly or via a connection conductor; and a relay connector that is attached to the relay substrate and is configured to bring an electrode formed on the rear substrate of the electronic module into contact with a relay conductor electrically connected to the terminal connection electrode via a wiring line formed on the relay substrate, so as to achieve electrical connection between the electrode of the rear substrate and the relay conductor. The relay connector has a connector base member attached to the relay substrate, the relay conductor provided on the connector base member, and a retaining member that sandwiches the rear substrate of the electronic module between the retaining member and the connector base member and is configured to press the electrode of the rear substrate against a contact part of the relay conductor.

The above-described electronic component unit may further include an external connection connector attached to the relay substrate. The external connection connector may have a terminal support provided with the external connection terminal and an accommodation tube that is attached to the relay substrate in a state in which the accommodation tube protrudes from an outer periphery of the relay substrate and accommodates the terminal support. The external connection terminal may be provided on a surface of the terminal support facing a mating contact insertion space secured in the accommodation tube, and a base end part of the external connection terminal located adjacent to the relay substrate may be electrically connected to the terminal connection electrode of the relay substrate.

The above-described electronic component unit may further include the external connection terminal to which an electric wire is electrically connected; and a connector housing that is configured to accommodate the external connection terminal and is assembled around (i.e., houses) the relay substrate and the relay connector. The external connection terminal may be electrically connected to the terminal connection electrode of the relay substrate via the connection conductor including the electric wire.

The connector base member may have a substrate support surface against which the rear substrate abuts, and the retaining member may have an engaging part that is configured to engage with the connector base member, and a retaining part that is configured to push the rear substrate into the substrate support surface in a state in which the engaging part is engaged with the connector base member.

In the above-described electronic component unit, $D1 \geq D2$ may be satisfied in a case where a length of a first diagonal line on a front end surface of the electronic element of the electronic module is D1 and a length of a second diagonal line of the rear substrate in a cross-section intersecting (perpendicular to) a longitudinal direction of the rear substrate is D2.

According to the electronic component unit according to the above embodiments of the present invention, it is possible to simply and easily perform an electrical connection between the electronic module such as the imaging module and other devices (relay substrate) without using a receptacle and a plug inserted and fitted into the receptacle. Additionally, according to the electronic component unit according to the above embodiments of the present invention, the electrical connection between the electronic module and the relay conductor can be easily realized by simply pressing the rear substrate of the electronic module against the contact part of the relay conductor of the relay connector by the retaining member of the relay connector. As a result, the electrical connection between the electronic module and the relay substrate can be simply realized via the relay conductor of the relay connector.

Additionally, according to the electronic component unit according to the above embodiments of the present invention, by adopting the rear substrate of the electronic module having a size capable of being inserted into the tube accommodating the electronic element and the electric cable, for example, it is possible to use the tube having as small a diameter as possible within a range in which the electronic element of the electronic module can be accommodated.

DETAILED DESCRIPTION

Hereinafter, electronic component units according to embodiments of the present invention will be described with reference to the drawings.

First Embodiment

First, an electronic component unit of a first embodiment according to the present invention will be described.

Figure 1:
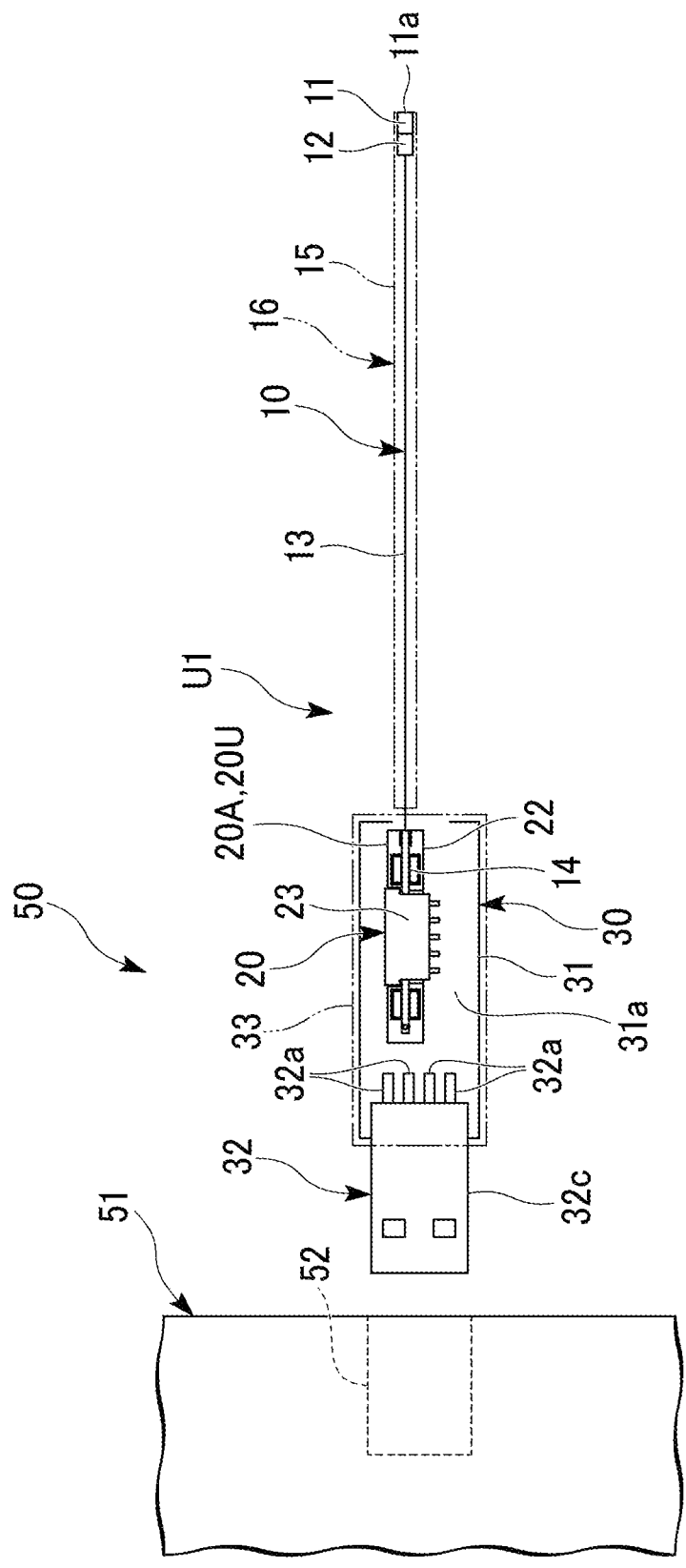
FIG. 1 is a view illustrating an example of an electronic component unit (imaging unit) and an electronic endoscope system according to a first embodiment of the present invention.

The electronic component unit U1 illustrated in FIG. 1 is an imaging unit that can be used as a part of a videoscope device of an electronic endoscope system 50.

As illustrated in FIG. 1, the electronic component unit U1 includes an imaging module 10 which is an electronic module including an imaging element 11 (electronic element), and a relay unit 30 that electrically connects an electric circuit of the imaging module 10 to an external circuit.

Figure 2:
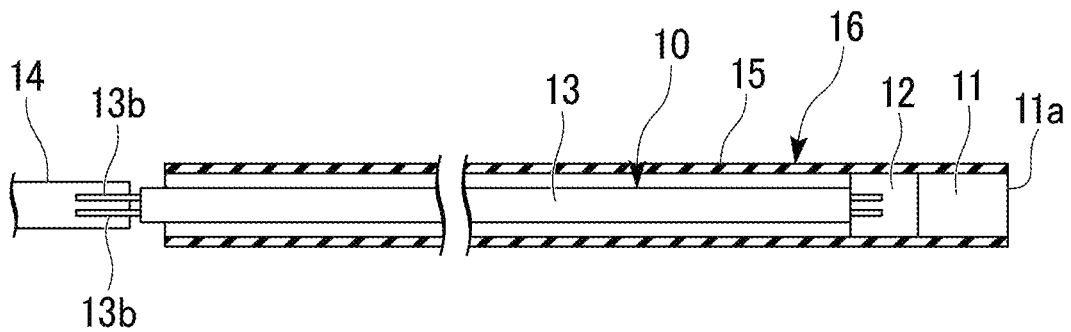
FIG. 2 is a cross-sectional view illustrating the configuration of an imaging module of the electronic endoscope system of FIG. 1.

As illustrated in FIGS. 1 and 2, the imaging module 10 includes the imaging element 11 (electronic element), a wiring substrate 12 on which the imaging element 11 is mounted (hereinafter, also referred to as a head-side substrate), an electric cable 13 electrically connected to the imaging element 11 via a wiring line (not illustrated) of the head-side substrate 12, and a rear substrate 14 that is electrically connected to a rear end of the electric cable 13 opposite to a front end connected to the wiring line of the head-side substrate 12.

Additionally, FIG. 2 illustrates a tube-attached module 16 in which the imaging element 11, the head-side substrate 12, and the electric cable 13 of the imaging module 10 are accommodated in a resin tube 15 having excellent flexibility.

However, the rear substrate 14 of the imaging module 10 is not accommodated in the tube 15 and is exposed in a state in which the rear substrate 14 protrudes outward from the end (rear end) of the tube 15.

As illustrated in FIG. 1, the relay unit 30 includes a relay substrate 31, a relay connector 20 attached to one main surface 31a of the relay substrate 31, and an external connection connector 32 attached to the relay substrate 31.

Additionally, the relay unit 30 of FIG. 1 also has a substrate accommodation housing 33 assembled around the relay substrate 31 and the relay connector 20. The substrate accommodation housing 33 accommodates the relay substrate 31 and the relay connector 20.

Figure 5:
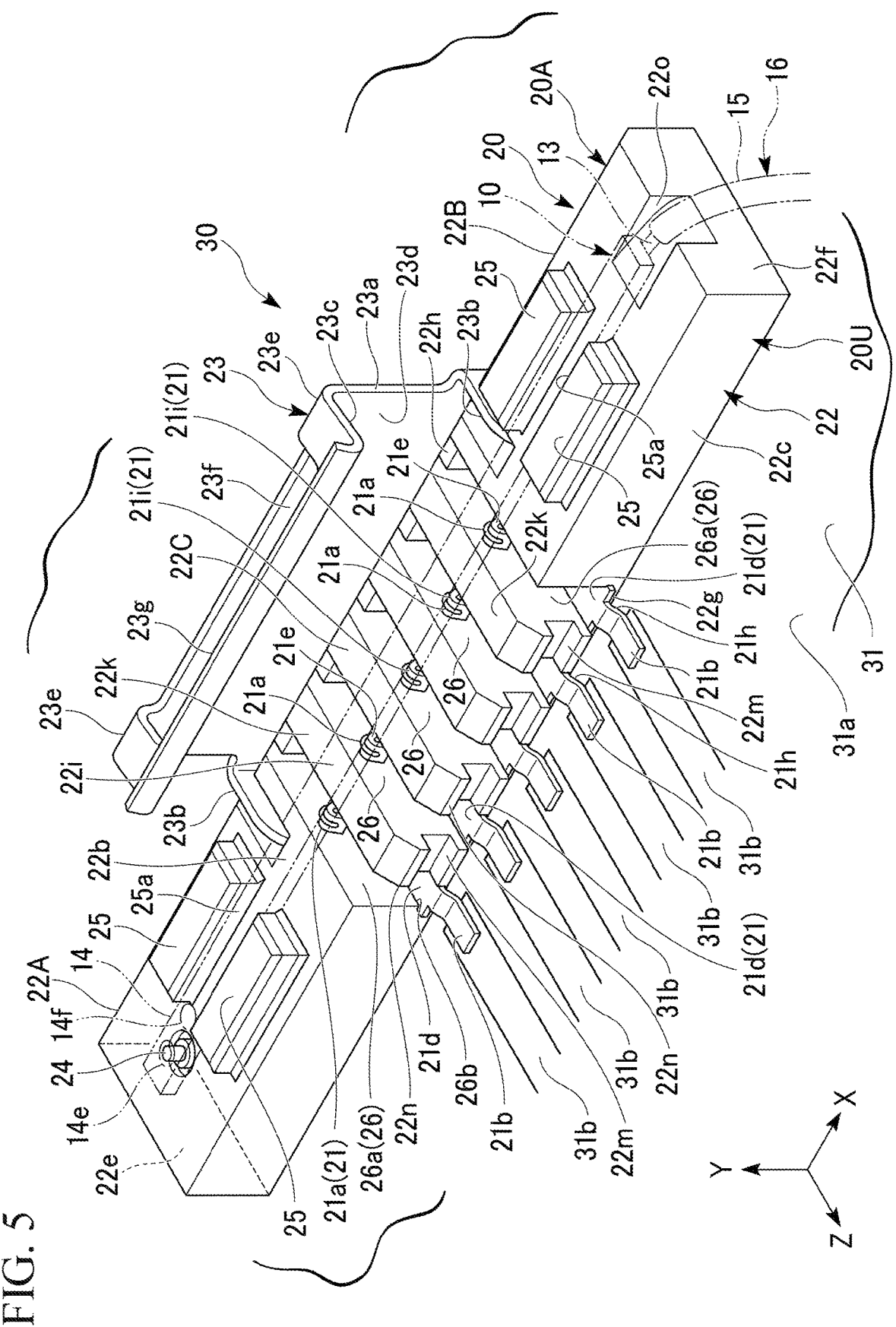
FIG. 5 is a perspective view illustrating a relay connector of the relay unit of the electronic component unit of FIG. 1 and illustrating a state in which a retaining member is opened with respect to a housing.

FIG. 5 illustrates a perspective view of the relay connector 20 of the relay unit 30. As illustrated in FIG. 5, the relay connector 20 has a plurality of contacts 21 (relay conductors), a housing 22 that holds the contacts 21, and a retaining member 23 rotatably pivoted by the housing 22. In FIG. 5, the retaining member 23 is in an open state with respect to the housing 22.

Figure 6:
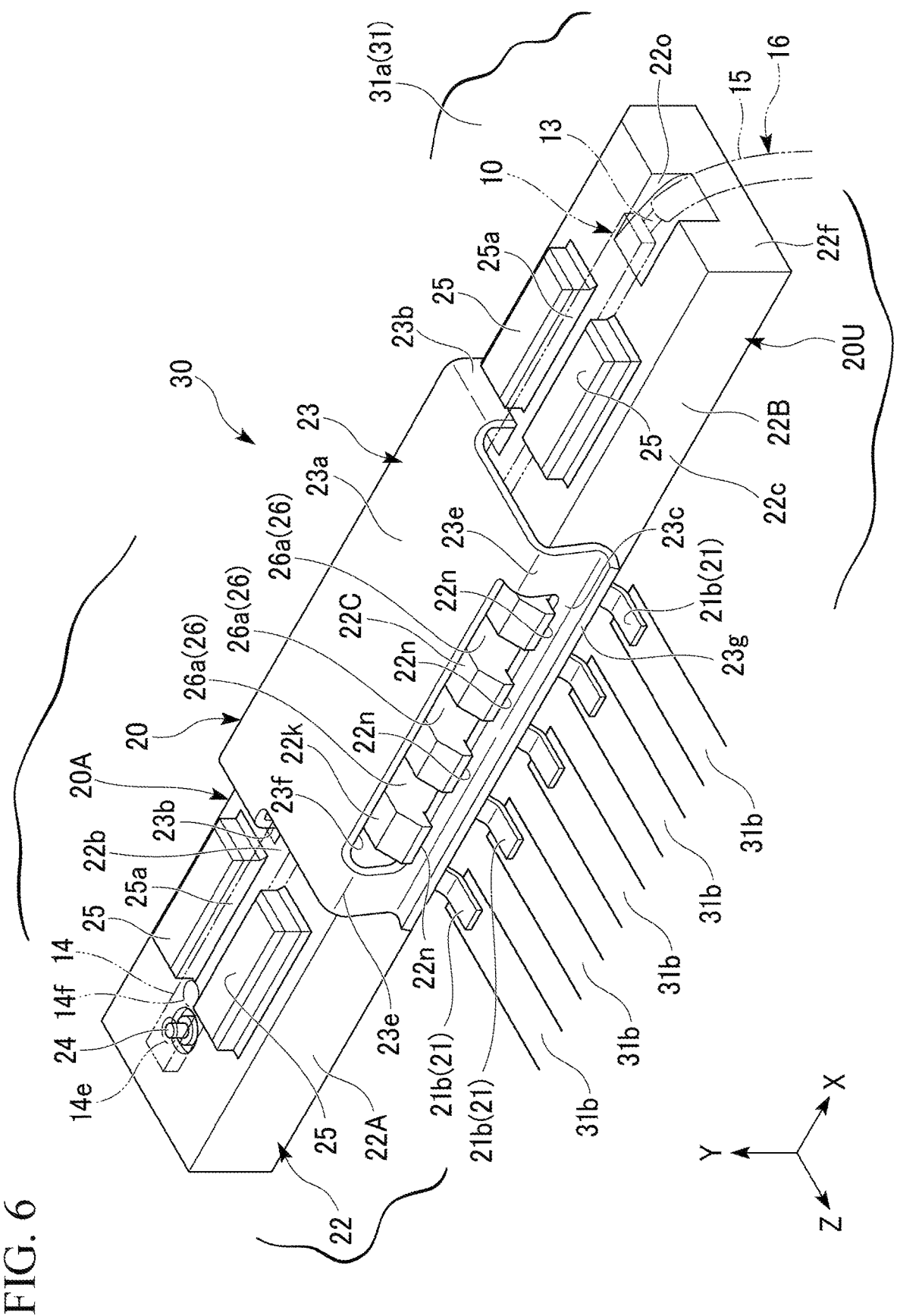
FIG. 6 is a perspective view illustrating a state in which a rear substrate of the electronic module is sandwiched and fixed between the retaining member closed and brought into a keep-closed and locked state with respect to the housing and the housing, regarding the relay connector of FIG. 5.

FIG. 6 illustrates a perspective view of the relay connector 20 illustrated in FIG. 5 in a state in which the retaining member 23 is closed with respect to the housing 22. As illustrated in FIG. 6, the rear substrate 14 of the electronic module 10 is sandwiched and fixed between the retaining member 23 and the housing 22.

Here, a direction in which the housing 22 of the relay connector 20 extends is referred to as a longitudinal direction (X direction), and a first end surface 22e side of the housing 22 in the longitudinal direction is a first end part, and a second end surface 22f side in the longitudinal direction is a second end part. A direction in which the relay substrate 31, the housing 22, and the rear substrate 14 are stacked is referred to as an up-down direction (Y direction), and the rear substrate 14 side in the up-down direction is an upper side and the relay substrate 31 side in the up-down direction is a lower side. A direction orthogonal to the longitudinal direction and the up-down direction is referred to as a front-rear direction (Z direction). A side on which a connection part 21b of each contact 21 extends in the front-rear direction is referred to as a front side, and a side opposite thereto is referred to as a rear side.

Additionally, the relay connector 20 also has a positioning part (a longitudinal positioning part 24 and a width-direction positioning part 25) to be described below. The rear substrate 14 of the imaging module 10 can be positioned with respect to the housing 22 by the positioning parts.

The relay connector 20 has a connector base member 20A in which the longitudinal positioning part 24 and the width-direction positioning part 25 are provided on the housing 22.

Additionally, the relay connector 20 has a base unit 20U in which the contacts 21 are provided on the connector base member 20A.

Figure 7:
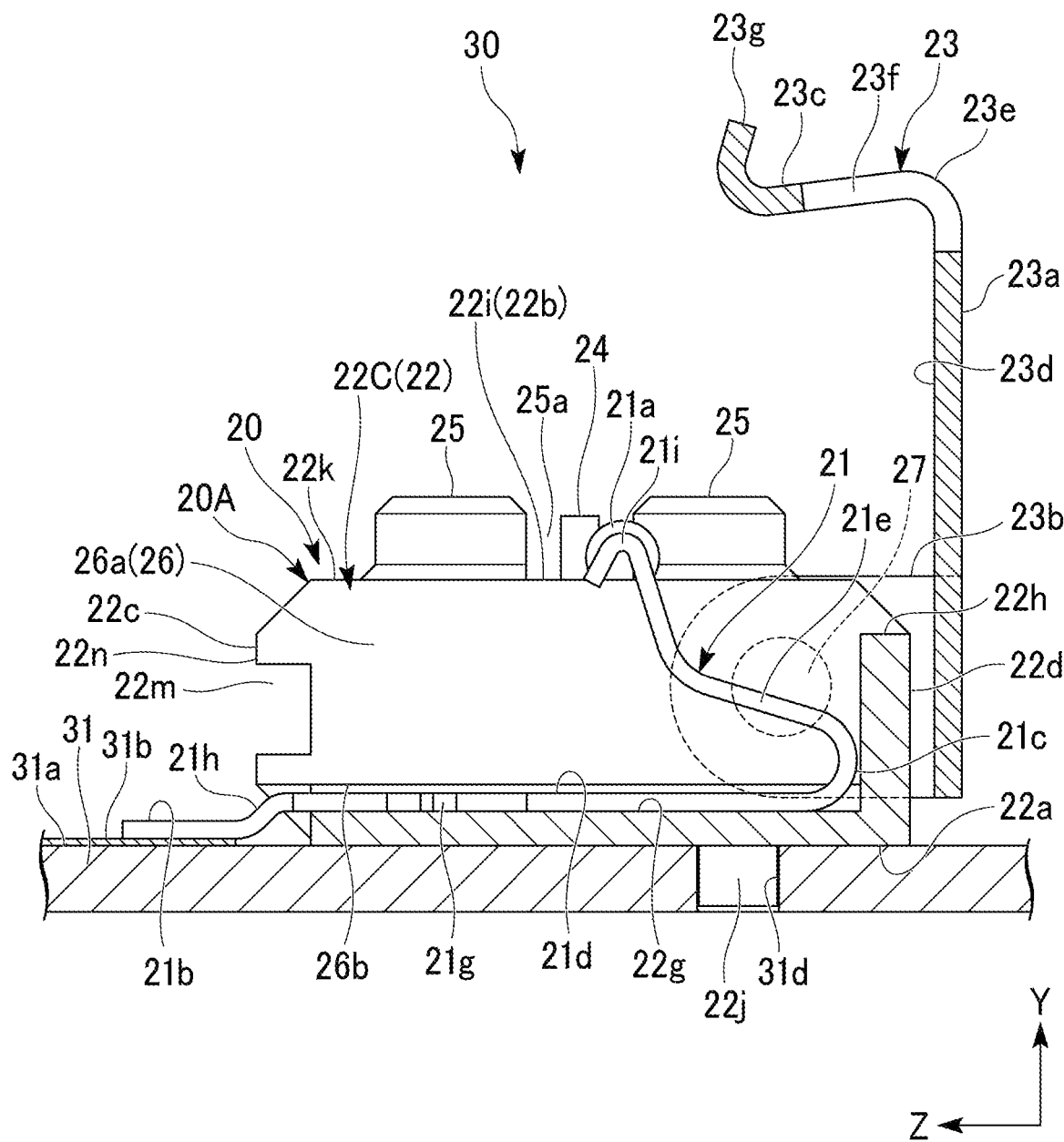
FIG. 7 is a cross-sectional view illustrating the vicinity of a contact accommodation groove of the relay connector of FIG. 5.
Figure 8:
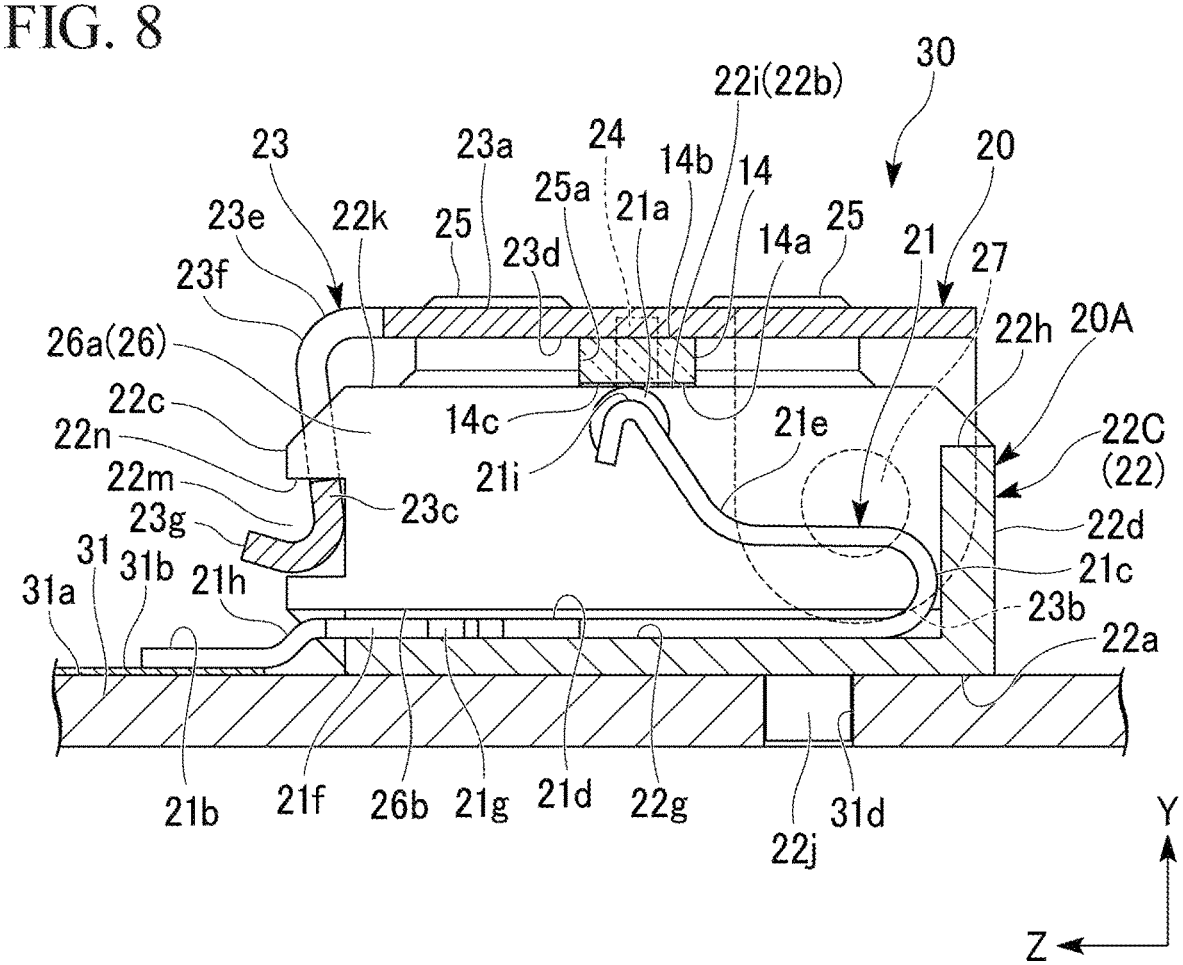
FIG. 8 is a cross-sectional view illustrating the vicinity of the contact accommodation groove of the relay connector of FIG. 6.

FIG. 7 illustrates a cross-sectional view of the vicinity of the contact accommodation groove of the relay connector of FIG. 5. FIG. 8 illustrates a cross-sectional view of the vicinity of a contact accommodation groove 26 of the relay connector 20 of FIG. 6. As illustrated in FIG. 8, the contact 21 of the relay connector 20 has a contact part 21a and a connection part 21b. The contact part 21a comes into contact with an electrode 14c formed on the rear substrate 14 of the imaging module 10. The connection part 21b is electrically connected to a wiring line 31b of the relay substrate 31 by soldering.

The retaining member 23 of the relay connector 20 sandwiches the rear substrate 14 of the imaging module 10 with the housing 22 and presses an electrode 14c of the rear substrate 14 against the contact part 21a of the contact 21. Accordingly, the contact part 21a comes into contact with the electrode 14c formed on the rear substrate 14 of the imaging module 10 and is electrically connected to the electrode 14c.

The electrical connection between the connection part 21b of the contact 21 and the wiring line 31b of the relay substrate 31 is not limited to the soldering and may be realized by, for example, bending of a fixing metal piece provided on the relay substrate 31, mechanical fixing in which the connection part 21b is pushed into the wiring line 31b by a clip capable of being fitted and fixed to the relay substrate 31, or the like.

The relay connector 20 electrically connects the electric circuit of the imaging module 10 including the electrode 14c of the rear substrate 14 to the wiring line 31b of the relay substrate 31 via the contact 21.

The electronic endoscope system 50 illustrated in FIG. 1 has a video processing display device 51 including a monitor.

The video processing display device 51 is provided with a receptacle 52 into which the external connection connector 32 of the relay unit 30 can be inserted and is attachable and detachable.

The external connection connector 32 of the relay unit 30 is inserted and fitted into the receptacle 52 of the video processing display device 51. Accordingly, an electric circuit of the video processing display device 51 and an electric circuit of the relay substrate 31 including the wiring line 31b are electrically connected to each other.

The relay unit 30 electrically connects the circuit of the imaging module 10 and the wiring line 31b of the relay substrate 31 via the contact 21 of the relay connector 20. Moreover, by inserting and fitting the external connection connector 32 into the receptacle 52 of the video processing display device 51, the relay unit 30 electrically connects the electric circuit (external circuit) of the video processing display device 51 to the electric circuit of the imaging module 10.

Figure 3:
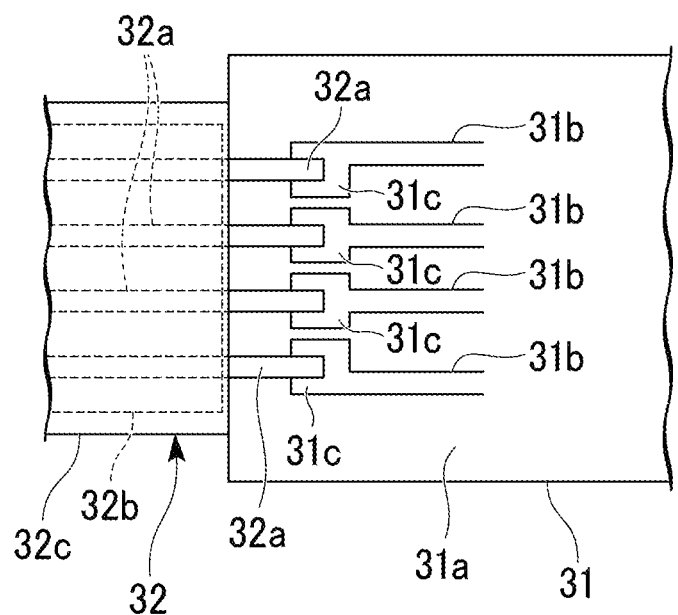
FIG. 3 is a plan view illustrating the vicinity of a terminal connection electrode of a relay substrate to which an external connection terminal of an external connection connector of the electronic component unit (imaging unit) of FIG. 1 is electrically connected.

FIG. 3 illustrates a state in which an external connection terminal 32a of the external connection connector 32 is connected to a terminal connection electrode 31c of the relay substrate 31.

Figure 4:
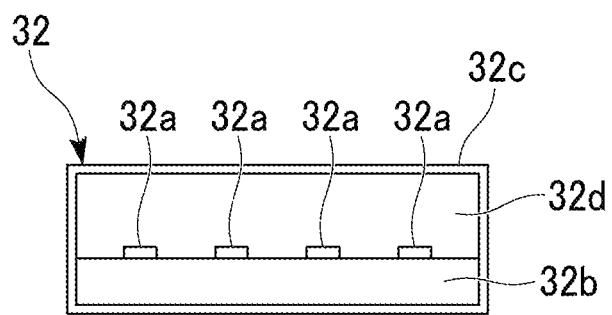
FIG. 4 is a view illustrating a configuration in which the external connection connector of the electronic component unit (imaging unit) of FIG. 1 is seen from a tip (a protruding end with respect to the relay substrate) side.

The terminal connection electrode 31c is electrically connected to the wiring line 31b of the relay substrate 31. In FIG. 3, the external connection terminal 32a is directly connected to the terminal connection electrode 31c. However, the external connection terminal 32a is not limited to this and may be electrically connected to the terminal connection electrode 31c via a connection conductor. FIG. 4 illustrates a configuration in which the external connection connector 32 is seen from a tip side thereof. As illustrated in FIGS. 3 and 4, the external connection connector 32 has the external connection terminal 32a, a terminal support 32b to which the external connection terminal 32a is fixed, and an accommodation tube 32c that accommodates the terminal support 32b together with the external connection terminal 32a.

As illustrated in FIG. 4, the accommodation tube 32c has an oblong cross-sectional shape and is formed in a flat rectangular frame shape. As illustrated in FIG. 1, the first end part (base end part) of the accommodation tube 32c on one side in the axial direction is fixed to an outer peripheral part of the main surface 31a of the relay substrate 31. The accommodation tube 32c is attached to the relay substrate 31 in a state where a portion other than the base end part protrudes outward from an outer periphery of the relay substrate 31. Additionally, the accommodation tube 32c is attached to the relay substrate 31 such that an axis thereof is parallel to the main surface 31a of the relay substrate 31.

The terminal support 32b illustrated in FIG. 4 is formed in a plate shape. The terminal support 32b is fixed to the accommodation tube 32c such that one surface thereof is made to abut against an inner surface of the accommodation tube 32c.

As illustrated in FIG. 4, a mating contact insertion space 32d is secured inside the accommodation tube 32c. A contact on the receptacle side into which the external connection connector 32 is inserted and fitted is inserted into the mating contact insertion space 32d.

In FIG. 4, the mating contact insertion space 32d is secured on the side of the terminal support 32b opposite to a surface, which is made to abut against the inner surface of the accommodation tube 32c, via the terminal support 32b. The terminal support 32b has a surface facing the mating contact insertion space 32d and surfaces abutting against the inner surface of the accommodation tube 32c. In the terminal support 32b, the surface facing the mating contact insertion space 32d faces one of the surfaces abutting against the inner surface of the accommodation tube 32c.

The external connection terminal 32a is provided on the surface of the terminal support 32b toward the mating contact insertion space 32d.

When the external connection terminal 32a is inserted and fitted into the receptacle, the external connection terminal 32a comes into contact with a receptacle-side contact inserted into the mating contact insertion space 32d and is brought into a state in which the external connection terminal 32a is an electrically connected state with an external circuit electrically connected to the receptacle-side contact.

The external connection terminal 32a illustrated in FIGS. 3 and 4 is a strip-shaped metal piece formed of a material having high electrical conductivity (good conductor) such as copper.

As illustrated in FIG. 3, the external connection terminal 32a is an extending part (a base end part of the external connection terminal 32a) that protrudes from an opening part adjacent to the base end part of the accommodation tube 32c onto the main surface 31a of the relay substrate 31. The base end part of the external connection terminal 32a is electrically connected to the terminal connection electrode 31c formed on the main surface 31a of the relay substrate 31 by soldering. The external connection terminal 32a is electrically connected to the contact 21 of the relay connector 20 via the terminal connection electrode 31c and the wiring line 31b of the relay substrate 31. In addition, the base end part of the external connection terminal 32a may be electrically connected to the terminal connection electrode 31c of the relay substrate 31 and may not protrude onto the main surface 31a of the relay substrate 31.

By inserting and fitting the external connection connector 32 into the receptacle 52 of the video processing display device 51 (refer to FIG. 1), the external connection terminal 32a of the external connection connector 32 comes into contact with the contact of the receptacle 52 and is electrically connected to the electric circuit of the video processing display device 51 via the contact of the receptacle 52.

Therefore, by inserting and fitting the external connection connector 32 into the receptacle 52 of the video processing display device 51, the relay unit 30 electrically connects the contact 21 of the relay connector 20 to the electric circuit of the video processing display device 51.

The accommodation tube 32c of the external connection connector 32 illustrated in FIGS. 3 and 4 is formed of a conductive metal. Accordingly, the accommodation tube 32c servers as an electromagnetic wave shield cover.

The accommodation tube 32c can be grounded, for example, by bringing the external connection connector 32 into contact with a grounding contact of the inserted and fitted receptacle.

In addition, although the accommodation tube 32c is formed of the conductive metal, the present invention is not limited to this and the accommodation tube 32c may be made of, for example, plastic.

As the accommodation tube 32c, accommodation tubes (shield frames) having various shapes of connectors adapted to the universal serial bus (USB) standard can be adopted.

The accommodation tube 32c is not limited to the flat rectangular frame shape (refer to FIG. 4).

Next, the relay connector 20 of the relay unit 30 will be described in more detail.

In addition, the relay connector 20 will be described with reference to FIGS. 5 to 8 with an upper side of a paper surface in the Z direction as the top and the lower side of the paper surface as the bottom.

The housing 22 of the relay connector 20 illustrated in FIG. 5 is a resin plate-shaped member. The housing 22 has electrical insulating properties.

Additionally, the housing 22 illustrated in FIG. 5 is formed in a plate shape extending in the longitudinal direction.

As illustrated in FIG. 5, the housing 22 has a contact placement region 22C and pedestal parts (a first pedestal part 22A and a second pedestal part 22B) on both sides of the contact placement region 22C, in the longitudinal direction. A plurality of the contact accommodation grooves 26 that accommodate a plurality of contacts 21 respectively are formed in the contact placement region 22C.

The contact placement region 22C is located at a central part of the housing 22 in the longitudinal direction.

The first pedestal part 22A and the second pedestal part 22B are portions on both sides of the contact placement region 22C in the longitudinal direction of the housing 22.

FIGS. 7 and 8 illustrate cross-sectional views of the vicinity of a contact accommodation groove 26 of the relay connector 20. FIG. 7 illustrates a state in which the retaining member 23 is open with respect to the housing 22, and FIG. 8 illustrates a state in which the retaining member 23 is closed with respect to the housing 22. As illustrated in FIGS. 7 and 8, the housing 22 has a flat bottom surface 22a abutting against the main surface 31a of the relay substrate 31 so as to overlap each other, and a substrate support surface 22b that is an upper surface formed parallel to the bottom surface 22a on the side opposite to the bottom surface 22a.

As illustrated in FIG. 8, the rear substrate 14 of the imaging module 10 is mounted on the substrate support surface 22b.

A spacing direction (the up-down direction in FIGS. 5, 7, and 8) between the bottom surface 22a and the substrate support surface 22b of the housing 22 is hereinafter also referred to as a height direction.

In the cross-sections perpendicular to the longitudinal direction of the housing 22 illustrated in FIGS. 7 and 8, the housing 22 has a front surface 22c and a rear surface 22d that are parallel to the height direction. In the contact accommodation groove 26 of the housing 22, as seen from a direction perpendicular to the height direction, the front surface 22c is a side surface on one side and the rear surface 22d is a side surface opposite to the front surface 22c. That is, the front surface 22c and the rear surface 22d of the housing 22 face each other in the front-rear direction.

In addition, as illustrated in FIG. 5, hereinafter, out of end surfaces on both sides of the housing 22 in the longitudinal direction, an end surface 22e disposed on the side closer to the first pedestal part 22A is also referred to as a first end surface, and an end surface 22f disposed on the side closer to the second pedestal part 22B is a second end surface.

As illustrated in FIGS. 5, 7, and 8, the contact accommodation groove 26 of the contact placement region 22C of the housing 22 is formed by being recessed from the substrate support surface 22b of the housing 22 toward the bottom surface 22a in the up-down direction. Additionally, in the front-rear direction, the contact accommodation groove 26 is formed so as to be recessed toward the rear surface 22d of the housing 22 and be open only to the front surface 22c of the housing 22.

The housing 22 has a groove bottom wall 22g on a lower side of the contact accommodation groove 26. A surface on the lower side of the groove bottom wall 22g forms a part of the bottom surface 22a. The contact accommodation groove 26 is formed in a range from the substrate support surface 22b of the housing 22 to the groove bottom wall 22g in the height direction of the housing 22.

The housing 22 also has a groove rear wall 22h that blocks a housing rear surface 22d of the contact accommodation groove 26 in the front-rear direction.

The plurality of contact accommodation grooves 26 of the housing 22 are formed so as to extend perpendicularly to the longitudinal direction of the housing 22, respectively. Additionally, the plurality of contact accommodation grooves 26 are formed parallel to each other in the contact placement region 22C of the housing 22.

The plurality of contact accommodation grooves 26 of the housing 22 are placed at predetermined intervals in the longitudinal direction. The interval direction (arrangement pitch direction) between the contact accommodation grooves 26 coincides with the longitudinal direction of the housing 22.

A plurality of contacts 21 accommodated in the respective contact accommodation grooves 26 one by one are placed at predetermined intervals in the longitudinal direction of the housing 22. The interval direction (arrangement pitch direction) between the plurality of contacts 21 provided in the housing 22 coincides with the longitudinal direction of the housing 22.

Figure 9:
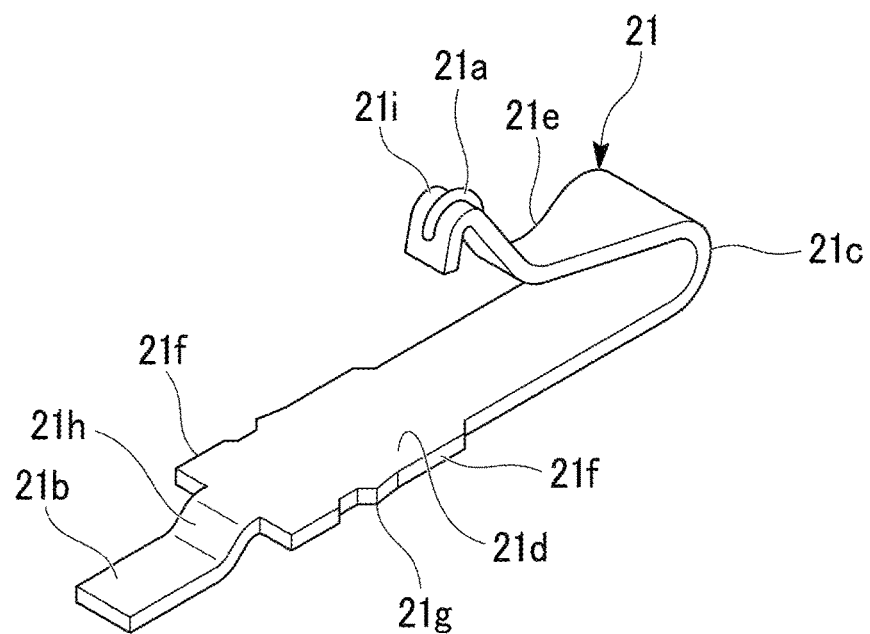
FIG. 9 is a perspective view illustrating a contact of the relay connector of FIG. 5.

As illustrated in FIGS. 7, 8, and 9, the contact 21 is an integrally molded product formed by a single metal strip.

The material of the metal strip that forms the contact 21 is, for example, a conductor metal such as copper or aluminum.

A bent part 21c (hereinafter, also referred to as a central bent part) formed by bending the metal strip in a plate thickness direction is formed at a longitudinal central part of the metal strip.

The contact 21 has a main plate part 21d and a movable plate part 21e that are connected by the central bent part 21c in the longitudinal direction of the metal strip. The movable plate part 21e extends from the central bent part 21c with an acute opening angle secured with respect to the main plate part 21d. The movable plate part 21e is inclined with respect to the main plate part 21d.

As illustrated in FIGS. 7, 8, and 9, the main plate part 21d of the contact 21 is formed so as to extend linearly from the central bent part 21c.

As illustrated in FIGS. 7 and 8, the main plate part 21d of the contact 21 (specifically, one surface of the main plate part 21d) is placed on the groove bottom wall 22g of the housing 22. The central bent part 21c of the contact 21 is placed in the vicinity of the groove rear wall 22h of the housing 22. The contact 21 is accommodated in the contact accommodation groove 26 in a state in which the movable plate part 21e extending from the central bent part 21c is located above the main plate part 21d.

As illustrated in FIG. 9, an overhanging part 21f is formed at a tip part opposite to the central bent part 21c in an extending direction of the main plate part 21d of the contact 21. The overhanging part 21f is wider than the main plate part 21d in the width direction of the metal strip. For this reason, the overhanging part 21f protrudes to both sides of the metal strip in the width direction. Additionally, the main plate part 21d of the contact 21 is also formed with a fixing projection 21g that protrudes from the overhanging part 21f so as to be separated from each other in a plate width direction of the main plate part 21d.

The fixing projection 21g is formed in a chevron shape in which the protruding dimension of the metal strip in the width direction increases along a direction from the connection part 21b and the central bent part 21c, which are both ends in the extending direction of the main plate part 21d of the contact 21, toward the central part.

The contact accommodation groove 26 of the housing 22 illustrated in FIGS. 5, 7, and 8 has a main groove part 26a and a guide groove 26b. The main groove part 26a is recessed from the substrate support surface 22b of the housing 22 to the groove bottom wall 22g in the up-down direction. The guide groove 26b is formed in a groove bottom part of the main groove part 26a. The guide grooves 26b are formed on inner side surfaces on both sides of the main groove part 26a of the contact accommodation groove 26 in a groove width direction (coinciding with the longitudinal direction of the housing 22). The guide groove 26b is formed to extend from the front surface 22c of the housing 22 toward the groove rear wall 22h.

The overhanging part 21f and the fixing projection 21g of the main plate part 21d of the contact 21 are inserted from the front surface 22c side of the housing 22 into a space formed by the groove bottom part of the main groove part 26a and the two guide grooves 26b facing each other in the longitudinal direction. That is, the overhanging part 21f and the fixing projection 21g of the main plate part 21d of the contact 21 are inserted into the guide groove 26b. Accordingly, the overhanging part 21f and the fixing projection 21g of the main plate part 21d of the contact 21 come into contact with an inner surface of the guide groove 26b, such that the floating thereof from the groove bottom wall 22g of the housing 22 (the contact 21 is separated upward) is restricted.

In order to accommodate the contact 21 in the contact accommodation groove 26, first, the contact 21 is placed on the side closer to the front surface 22c of the housing 22 such that the central bent part 21c of the contact 21 and the front surface 22c of the housing 22 face each other in the front-rear direction. The contact 21 is pushed into the contact accommodation groove 26 from the side closer to the front surface 22c of the housing 22 while the main plate part 21d is slidingly moved onto the upper surface of the groove bottom wall 22g. Accordingly, the contact 21 is accommodated in the contact accommodation groove 26.

When the contact 21 is pushed in from the side closer to the front surface 22c of the housing 22 and is accommodated in the contact accommodation groove 26, the overhanging part 21f and the fixing projection 21g are inserted into the guide groove 26b. The fixing projections 21g protrudes to both sides of the metal strip of the main plate part 21d of the contact 21 in the width direction, and the width of the fixing projection 21g in the width direction of the metal strip is slightly larger than the distance between the inner surfaces of two guide grooves 26b facing each other in the longitudinal direction at a lower part of the contact accommodation groove 26. The main plate part 21d of the contact 21 inserted into the contact accommodation groove 26 is fixed to the housing 22 as protruding ends of the fixing projections 21g on both sides thereof are brought into pressure contact with the respective inner surfaces of the guide grooves 26b of the contact accommodation groove 26 facing each other in the longitudinal direction. Additionally, as a result, the contact 21 is held at a predetermined position of the housing 22.

In addition, the width of the fixing projection 21g in the width direction of the metal strip may be larger than the width of the contact accommodation groove 26 (the distance between the inner surfaces of the contact accommodation groove 26 facing each other the longitudinal direction) and smaller than the distance between the inner surfaces of the two guide grooves 26b facing each other in the longitudinal direction. Accordingly, it is possible to restrict the upward separation of the contact 21 from the groove bottom wall 22g of the housing 22.

The structure for holding the main plate part 21d of the contact 21 at a predetermined position of the housing 22 (contact holding structure) is not limited to the structure in which the fixing projection 21g of the contact 21 is brought into pressure contact with the inner surface of the guide groove 26b.

As the contact holding structure, for example, it is also possible to adopt a configuration in which the main plate part 21d is held at a predetermined position of the housing 22 by the engagement between an elastic locking piece (housing lance) protruding from the inner surface of the contact accommodation groove 26 of the housing 22 and an engaging protrusion or engaging recess formed in the main plate part 21d of the contact 21.

The contact 21 includes an extending part 21h and a connection part 21b. The central bent part 21c is placed at one end part of the main plate part 21d in the extending direction of the main plate part 21d, and the extending part 21h and the connection part 21b are placed at the other end part of the main plate part 21d in the extending direction. The movable plate part 21e is bent upward with respect to the main plate part 21d via the central bent part 21c. The extending part 21h is bent toward the side (lower side) opposite to the movable plate part 21e and extends to be inclined at an inclination angle of 45 degrees or less with respect to the main plate part 21d. The connection part 21b extends from the end of the extending part 21h opposite to a side that the main plate part 21d is positioned.

The extending part 21h and the connection part 21b are parts of the metal strip that forms the contact 21.

The extending part 21h is connected to the main plate part 21d in one end part of the extending part 21h, and is connected to the connection part 21b on the other end part thereof. The connection part 21b extends parallel to the main plate part 21d.

As illustrated in FIGS. 5 to 8, the connection part 21b of the contact 21 is soldered to the wiring line 31b formed on the main surface 31a of the relay substrate 31 in which the housing 22 of the relay part connector 20 is placed. Accordingly, the connection part 21b of the contact 21 is electrically connected to the wiring line 31b.

The entire contact 21 is electrically connected to the wiring line 31b of the main surface 31a of the relay substrate 31.

As illustrated in FIGS. 7 and 8, the connector base member 20A of the relay connector 20 has a fitting projection 22j that protrudes from the bottom surface 22a of the housing 22. The connector base member 20A is attached to the relay substrate 31 by inserting and fitting the fitting projection 22j of the housing 22 into a fitting hole 31d formed in the relay substrate 31 and causing the bottom surface 22a of the housing 22 to abut against the main surface 31a of the relay substrate 31.

Additionally, the connector base member 20A can secure a fixing force for the relay substrate 31 even by soldering the connection part 21b of the contact 21 inserted into each of the plurality of contact accommodation grooves 26 to the wiring line 31b of the relay substrate 31.

The contact part 21a of the contact 21 is formed at an end part (tip part) of the movable plate part 21e opposite to the central bent part 21c.

The tip part of the movable plate part 21e of the contact 21 illustrated in FIGS. 7, 8, and 9 has a tip bent part 21i formed in a chevron shape in which the movable plate part 21e is bent in the plate thickness direction and which is convex upward.

Specifically, the contact part 21a of the contact 21 illustrated in FIGS. 7, 8, and 9 is a rib-shaped protrusion that is formed on an external angle side of the tip bent part 21i of the movable plate part 21e, and extends in the extending direction of the movable plate part 21e.

In addition, the contact part 21a of the contact 21 is not limited to the rib-shaped protrusion formed at the tip part of the movable plate part 21e and can be appropriately changed. In the contact 21, the contact part 21a, which is a rib-shaped protrusion, may be omitted, and for example, the tip bent part 21i itself of the tip part of the movable plate part 21e may be used as the contact part.

As illustrated in FIG. 6, the retaining member 23 has a top plate (retaining part) 23a, a pair of shaft pivoting protruding pieces 23b, and an engaging plate piece 23c. The pair of pivoting protruding pieces 23b protrudes downward from the top plate 23a at the respective end parts of the top plate 23a in the longitudinal direction. The engaging plate piece 23c protrudes downward from the top plate 23a at a front end part of the top plate 23a in the front-rear direction.

The pair of pivoting protruding pieces 23b of the retaining member 23 is pivoted so as to be rotatable around an axis (rotational axis), which is parallel to the longitudinal direction of the housing 22 via a rotary shaft 27 provided at a rear part of the housing 22 (a portion on the side closer to the rear surface 22d in FIGS. 7 and 8), with respect to the housing 22.

The entire retaining member 23 rotates with respect to the housing 22 around the rotational axis via the pivoting protruding pieces 23b and the rotary shaft 27.

The top plate 23a of the retaining member 23 illustrated in FIGS. 5 and 6 is formed in a rectangular plate shape.

The end parts of the top plate 23a in the longitudinal direction are portions along one side of the outer periphery of the top plate 23a. The pair of pivoting protruding pieces 23b extends from the end parts of the top plate 23a in the longitudinal direction to one surface side (lower side in FIG. 6) of the top plate 23.

The retaining member 23 is rotatably pivoted on the housing 22 via the pivoting protruding pieces 23b formed at the end parts of the top plate 23a in the longitudinal direction.

The top plate 23a of the retaining member 23 is opened and closed with respect to a portion (a support surface 22i on the placement region) located in the contact placement region 22C of the substrate support surface 22b of the housing 22 by rotating the retaining member 23 with respect to the housing 22.

When the top plate 23a of the retaining member 23 is closed with respect to the contact placement region 22C, the surface of the top plate 23a that faces the contact placement region 22C is hereinafter also referred to as a retaining surface 23d.

The pivoting protruding pieces 23b and the engaging plate piece 23c protrude from the top plate 23a toward the retaining surface 23d of the top plate 23a.

The engaging plate piece 23c of the retaining member 23 illustrated in FIG. 6 is a plate piece that is formed to extend along the front end part of the top plate 23a in the front-rear direction. The engaging plate piece 23c is placed perpendicular to the top plate 23a. Additionally, the engaging plate piece 23c extends in the longitudinal direction of the housing 22.

As illustrated in FIGS. 5 and 6, only both end parts of the engaging plate piece 23c of the retaining member 23 in the extending direction are connected to the top plate 23a. In continuous parts 23e of the retaining member 23 illustrated in FIGS. 5 and 6, both end parts of the engaging plate piece 23c in the extending direction and the top plate 23a are connected to each other. An elongated hole-shaped engaging window hole 23f formed to extend parallel to the extending direction of the top plate 23a is formed between the two continuous parts 23e.

As illustrated in FIGS. 5 to 8, a plurality of groove partition walls 22k are placed between the plurality of contact accommodation grooves 26 of the housing 22. A locking groove 22m is formed in the groove partition wall 22k on the front surface 22c of the housing 22. The engaging plate piece 23c of the retaining member 23 closed with respect to the contact placement region 22C of the housing 22 is inserted into the locking groove 22m. In the relay connector 20 illustrated in FIG. 5, a plurality of the locking grooves 22m of the plurality of groove partition walls 22k of the housing 22 on the front surface 22c of the housing 22 are formed so as to be aligned with each other in the longitudinal direction of the housing 22. A contact accommodation groove 26 is placed between the locking grooves 22m in the longitudinal direction.

A locking protrusion 22n is formed above the locking groove 22m of the groove partition wall 22k of the housing 22. In the engaging plate piece 23c (an engaging part that engages with the housing 22) of the retaining member 23, the locking protrusion 22n is accommodated in the engaging window hole 23f. Accordingly, the engaging plate piece 23c is inserted into the locking grooves 22m. The locking protrusion 22n of the housing 22 accommodated in the engaging window hole 23f of the retaining member 23 engages with the engaging plate piece 23c of the retaining member 23. Accordingly, it is possible to prevent the retaining member 23 from rotating in an opening direction, because the upward displacement of the engaging plate piece 23c with respect to the housing 22 is restricted. The retaining member 23 accommodates the locking protrusion 22n (a locking part that locks the retaining member 23) of the groove partition wall 22k of the housing 22 in the engaging window hole 23f. By inserting the engaging plate piece 23c into the locking groove 22m, it is possible to maintain a closed state with respect to the contact placement region 22C.

The engaging plate piece 23c of the retaining member 23 serves as an engaging part that engages with the housing 22.

The state in which the retaining member 23 is closed with respect to the contact placement region 22C (closed state) indicates a state in which the top plate 23a of the retaining member 23 is closed with respect to the contact placement region 22C and the retaining surface 23d of the top plate 23a extends along the support surface 22i on the placement region. As illustrated in FIG. 6, the top plate 23a of the retaining member 23 in the closed state covers almost the entire support surface 22i on the placement region.

In a state in which the retaining member 23 is opened with respect to the contact placement region 22C (open state), the retaining surface 23d of the top plate 23a is positioned so as to secure an opening angle of 45 degrees or more with respect to the support surface 22i on the placement region, and the engaging plate piece 23c of the retaining member 23 is separated upward from the housing 22. In the open state, the work of setting the position of the rear substrate 14 of the imaging module 10 by the longitudinal positioning part 24 and the width-direction positioning part 25 on the housing 22 can be performed from the front surface 22c side of the housing 22.

In addition, in the retaining member 23 of the relay connector 20 of FIGS. 5 to 8, the retaining surface 23d of the top plate 23a can secure an opening angle of 90 degrees or more with respect to the support surface 22i on the placement region.

In the open state, the rear substrate 14 of the imaging module 10 can be placed (mounted or the like) on the substrate support surface 22b of the housing 22.

When the retaining member 23 in the open state is closed with respect to the contact placement region 22C, the rear substrate 14 of the imaging module 10 placed on the substrate support surface 22b of the housing 22 in the relay connector 20 is sandwiched between the top plate 23a of the retaining member 23 and the housing 22. In the retaining member 23, the engaging plate piece 23c is inserted into the locking groove 22m of the groove partition wall 22k of the housing 22, and the engaging plate piece 23c is engaged with the locking protrusion 22n of the groove partition wall 22k. Accordingly, it is possible to maintain the state in which the rear substrate 14 of the imaging module 10 is sandwiched between the top plate 23a and the housing 22.

Regarding the retaining member 23, the state in which the engaging plate piece 23c is inserted into the locking groove 22m of the groove partition wall 22k of the housing 22 and is locked to the locking protrusion 22n of the housing 22 is hereinafter referred to as a keep-closed and locked state.

The top plate 23a of the retaining member 23 in the keep-closed and locked state presses the rear substrate 14 of the imaging module 10 toward the support surface 22i on the placement region by the retaining surface 23d. That is, the top plate 23a serves as a retaining part that presses the rear substrate 14 against the support surface 22i on the placement region.

The locking groove 22m of the housing 22 illustrated in FIG. 5 is formed in the groove partition wall 22k (contact placement region 22C) of the housing 22 and is formed in the first pedestal part 22A and the second pedestal part 22B of the housing 22.

When the retaining member 23 is closed with respect to the contact placement region 22C, both end parts of the engaging plate piece 23c of the retaining member 23 in the extending direction are placed on the side closer to the housing front surface 22c of the contact accommodation grooves 26 located at both ends of the contact placement region 22C of the housing 22 in the longitudinal direction.

However, when the retaining member 23 is closed with respect to the contact placement region 22C, the engaging plate piece 23c of the retaining member 23 abuts against only the groove partition wall 22k of the housing 22 and is formed with such a dimension that the engaging plate piece 23c do not abut against the first pedestal part 22A and the second pedestal part 22A of the housing 22.

When the engaging plate piece 23c of the retaining member 23 is inserted into the locking groove 22m of the groove partition wall 22k of the housing 22, the engaging plate piece does not interfere with the first pedestal part 22B and the second pedestal part 22B. For this reason, the engaging plate piece 23c can be smoothly inserted into the locking groove 22m.

In addition, the housing 22 is not limited to the configuration in which the locking groove 22m is formed in the groove partition wall 22k (contact placement region 22C). It is also possible to adopt a configuration in which the locking groove 22m is also formed on the front surface 22c of one or both of the first pedestal part 22A and the second pedestal part 22B in the housings 22.

In a case where the locking groove 22m is formed not only on the groove partition wall 22k (contact placement region 22C) but also on the front surface 22c of one or both of the first pedestal part 22A and the second pedestal part 22B in the housings 22, it is possible to adopt a configuration in which the engaging plate piece 23c of the retaining member 23 disposed in an end part in the extending direction along the longitudinal direction of the housing 22 is inserted into the locking groove 22m which is formed in one or both of the first pedestal part 22A and the second pedestal part 22B.

The retaining member 23 has an operating piece 23g provided at an end part of the engaging plate piece 23c opposite to the top plate 23a. The operating piece 23g protrudes to the side opposite to the top plate 23a in the plate thickness direction of the engaging plate piece 23c.

Even in a state in which the engaging plate piece 23c of the retaining member 23 is inserted into the locking groove 22m of the groove partition wall 22k of the housing 22, the operating piece 23g protrudes from the locking groove 22m toward the front surface 22c of the housing 22. For this reason, when a worker opens and closes the retaining member 23, it is possible to secure a portion to be pinched by fingers or the like.

By rotationally operating the retaining member 23 with respect to the housing 22 using the operating piece 23g, it is possible to simply perform the work of changing the retaining member 23 from the open state to the closed state with respect to the housing 22 and the keep-closed and locked state.

In the keep-closed and locked state, the retaining member 23 may be triggered by a tool inserted into a gap between the engaging plate piece 23c and the relay substrate 31. Accordingly, the state in which the engaging plate piece 23c is engaged with the locking protrusion 22n of the housing 22 (keep-closed and locked state) can be released.

The retaining member 23 of which the keep-closed and locked state is released can be brought into the open state by the rotational operation thereof with respect to the housing 22.

As illustrated in FIG. 5, the longitudinal positioning part 24 and the width-direction positioning part 25 of the connector base member 20A are provided so as to protrude upward from the substrate support surface 22b of the housing 22.

The longitudinal positioning part 24 of the connector base member 20A illustrated in FIG. 5 is provided on the first pedestal part 22A of the housing 22. Specifically, the longitudinal positioning part 24 in FIG. 5 is a positioning pin that is fixed to the first pedestal part 22A and protrudes upward from an upper surface of the first pedestal part 22A.

Hereinafter, in a case where the longitudinal positioning part 24 refers to the positioning pin, the longitudinal positioning part 24 is also referred to as a positioning pin 24.

Specifically, the width-direction positioning part 25 of the connector base member 20A illustrated in FIG. 5 is a rib-shaped protruding wall (protruding part) that protrudes upward from the upper surface of each of the first pedestal part 22A and the second pedestal part 22B of the housing 22.

Hereinafter, in a case where the width-direction positioning part 25 refers to the rib-shaped protruding wall, the width-direction positioning part 25 is also referred to as a rib-shaped protruding wall 25.

As illustrated in FIG. 5, a pair of rib-shaped protruding walls 25 extending in the longitudinal direction of the housing 22 is formed on the upper surface of each of the first pedestal part 22A and the second pedestal part 22B respectively.

In the front-rear direction, a substrate accommodation groove 25a is formed between the pair of rib-shaped protruding walls 25. The rear substrate 14 of the imaging module 10 provided on the substrate support surface 22b of the housing 22 is inserted into the substrate accommodation groove 25a. The substrate accommodation groove 25a between the pair of rib-shaped protruding walls 25 on the first pedestal part 22A is located on a virtual extension line of the substrate accommodation groove 25a between the pair of rib-shaped protruding walls 25 on the second pedestal part 22B.

The rib-shaped protruding walls 25 on both sides of the substrate accommodation groove 25a are placed on the substrate support surface 22b of the housing 22 and are separated from each other in the width direction (front-rear direction) perpendicular to the longitudinal direction of the housing 22.

In FIG. 5, the groove width of the substrate accommodation groove 25a, that is, the separation distance between the rib-shaped protruding walls 25 on both sides of the substrate accommodation groove 25a in the front-rear direction substantially coincides with the dimension of the elongated plate-shaped rear substrate 14 of the imaging module 10 in the width direction (the front-rear direction in the rear substrate 14 of FIG. 5)

The rear substrate 14 of the imaging module 10 is inserted into the substrate accommodation groove 25a between the respective rib-shaped protruding walls 25 of the first pedestal part 22A and the second pedestal part 22B. Accordingly, the rear substrate 14 is supported by the rib-shaped protruding walls 25 on both sides of each substrate accommodation groove 25a with an orientation extending in the longitudinal direction of the housing 22, and it is possible to set a position of the rear substrate 14 in the width direction of the substrate support surface 22b of the housing 22.

A jig hooking hole 14e (first jig hooking hole) is formed at an end part (rear end part) of the rear substrate 14 of the imaging module 10 on one side in the longitudinal direction.

As illustrated in FIG. 5, the positioning pin 24 of the connector base member 20A is inserted into the jig hooking hole 14e (first jig hooking hole) that is a through hole. Accordingly, the rear substrate 14 inserted into the substrate accommodation groove 25a between the rib-shaped protruding walls 25 of the first pedestal part 22A and the second pedestal part 22B is positioned in the longitudinal direction of the housing 22 (the longitudinal direction of the substrate support surface 22b).

The first jig hooking hole 14e of the rear substrate 14 may be used to attach an insertion jig such as a wire to the rear substrate 14 when the tube-attached module 16 is assembled by inserting the imaging module 10 into the tube 15.

When the tube-attached module 16 is assembled, the imaging module 10 is inserted into the tube 15 from the rear substrate 14.

Figure 10:
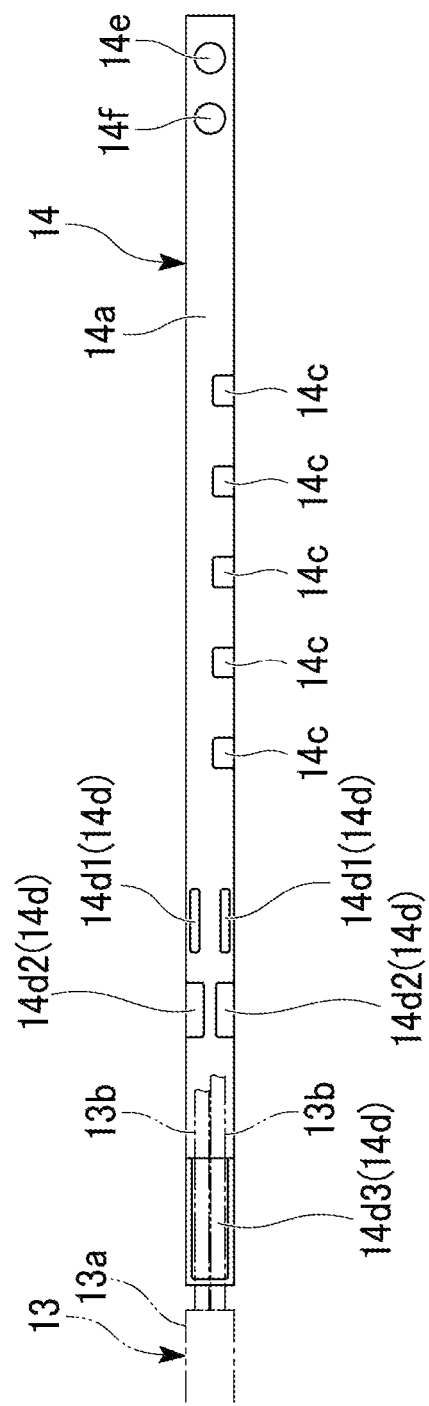
FIG. 10 is a view illustrating a first main surface of the rear substrate of the imaging module of the electronic component unit (imaging unit) of FIG. 1.

FIG. 10 illustrates the main surface 14a of the rear substrate 14 of the imaging module 10 of the electronic component unit U1 (imaging unit) of FIG. 1. In the longitudinal direction of the rear substrate 14, the imaging element 11 side of the rear substrate 14 is a first end part (front end part), and a rear end part (right end part in FIG. 10) opposite thereto is a second end part (rear end part). As illustrated in FIGS. 5 and 10, two jig hooking holes 14e and 14f (the first jig hooking hole 14e and a second jig hooking hole 14f) are formed at intervals in the longitudinal direction of the rear substrate 14 at the second end part of the rear substrate 14. The respective jig hooking holes 14e and 14f are through holes that penetrate the thickness of the rear substrate 14 and open to the main surfaces (the first main surface 14a and the second main surface 14b) on both sides of the rear substrate 14.

In addition, in this embodiment, only the first jig hooking hole 14e (pin locking hole) located behind the second jig hooking hole 14f is used to position the rear substrate 14 with respect to the housing 22 in the longitudinal direction of the housing 22.

As illustrated in FIG. 10, a plurality of the electrodes 14c are formed on one main surface (first main surface 14a) of the rear substrate 14 of the imaging module 10. Each electrode 14c comes into contact with the contact part 21a of the contact 21 of the connector base member 20A. The electrodes 14c are formed at a plurality of spots on the first main surface 14a in the longitudinal direction of the rear substrate 14. The plurality of electrodes 14c may be placed at intervals.

The rear substrate 14 illustrated in FIG. 10 is formed with the same number of electrodes 14c as the contacts 21 of the connector base member 20A. In FIG. 10, five electrodes 14c are formed.

An electric cable 13 of the imaging module 10 illustrated in FIGS. 2 and 10 has a configuration in which a plurality of conductors are accommodated inside an exterior covering 13a. However, as the electric cable 13, for example, it is possible to adopt a configuration in which a plurality of electric wires are accommodated in a protective tube, a coaxial cable (having a plurality of conductors), a single electric wire (having only one conductor), and the like.

In addition, the electric cable 13 of the imaging module 10 illustrated in FIGS. 2 and 10 is a signal cable that uses one or more of a plurality of conductors as signal lines.

As illustrated in FIG. 10, the conductor of the electric cable 13 is electrically connected to a conductor connection terminal 14d formed on the first main surface 14a of the rear substrate 14 of the imaging module 10 by soldering or the like. The conductor connection terminals 14d are formed at a plurality of spots (five spots in FIG. 10) of the first end part (front end part) of the rear substrate 14 of the imaging module 10.

Each conductor of the electric cable 13 is electrically connected to one of the conductor connection terminals 14d formed on the first main surface 14a of the rear substrate 14 of the imaging module 10, respectively.

The electric cable 13 illustrated in FIG. 10 has two coaxial cables 13b and one sub-conductor (not illustrated) that is a conductor accommodated inside the exterior covering 13a together with the coaxial cables 13b.

Figure 11:
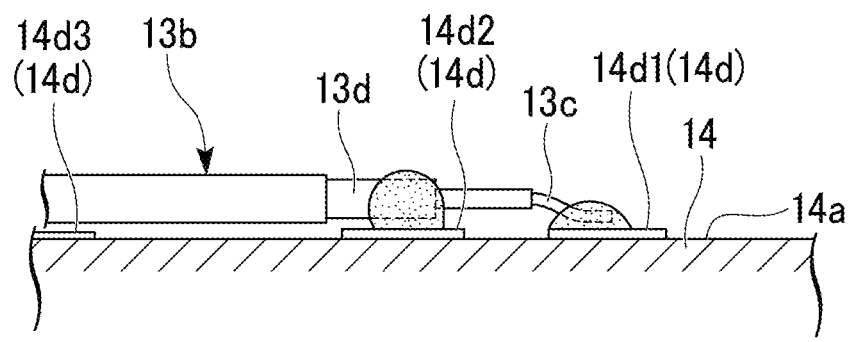
FIG. 11 is a view illustrating a connection state of a conductor of a coaxial cable of an electric cable of the imaging module with respect to a conductor connection terminal of the rear substrate of FIG. 10.

FIG. 11 illustrates a connection state between the conductor connection terminals 14d of the rear substrate 14 and the conductors of the coaxial cable 13b of the electric cable 13.

As illustrated in FIG. 11, the coaxial cable 13b has a central conductor 13c and an external conductor 13d.

The electric cable 13 illustrated in FIG. 10 has a total of five conductors, that is, the respective central conductors 13c and respective external conductors 13d of the two coaxial cables 13b and one sub-conductor.

As illustrated in FIGS. 10 and 11, the five conductor connection terminals 14d formed on the first main surface 14a of the rear substrate 14 of the imaging module 10 include two central conductor connection terminals 14d1 to which the central conductors 13c of the coaxial cables 13b are electrically connected, two external conductor connection terminals 14d2 to which the external conductors 13d of the coaxial cables 13b are electrically connected, and one sub-conductor connection terminal 14d3 to which the sub-conductor is electrically connected.

In the rear substrate 14, the same number of conductor connection terminals 14d as the electrodes 14c are formed. Each electrode 14c of the rear substrate 14 is electrically connected to one of the plurality of conductor connection terminals 14d via a wiring line (not illustrated) formed on the rear substrate 14, respectively.

The conductor of the electric cable 13 electrically connected to the conductor connection terminal 14d is electrically connected to the electrode 14c of the rear substrate 14 via wiring lines of the conductor connection terminal 14d and the rear substrate 14.

The plurality of electrodes 14c of the rear substrate 14 illustrated in FIG. 10 are formed by being arranged in a row in the longitudinal direction of the rear substrate 14. The placement intervals of the plurality of electrodes 14c of the rear substrate 14 in the longitudinal direction of the rear substrate 14 correspond to the placement intervals (arrangement pitch) of the plurality of contacts 21 (specifically, the contact parts 21a) of the connector base member 20A in the longitudinal direction of the housing 22.

In addition, in FIG. 5, the arrangement pitch of the contact accommodation grooves 26 in the longitudinal direction of the housing 22 and the arrangement pitch of the contacts 21 in the longitudinal direction of the housing 22 in the contact placement region 22C of the connector base member 20A are constant (regular intervals). However, the arrangement pitch of the contact accommodation grooves 26 and the arrangement pitch of the contacts 21 may not be constant (regular intervals).

As illustrated in FIG. 8, the rear substrate 14 of the imaging module 10 is placed on the substrate support surface 22b with such an orientation that the first main surface 14a faces the substrate support surface 22b (upper surface) of the housing 22.

Each electrode 14c of the rear substrate 14 of the imaging module 10 is positioned with respect to the housing 22 by the positioning pin 24 and the rib-shaped protruding wall 25 on the housing 22. Accordingly, the electrodes 14c are aligned with positions where the electrodes 14c are capable of abutting against the contact parts 21a of the contacts 21 of the connector base member 20A.

The rear substrate 14 is positioned with respect to the housing 22 by the positioning pin 24 and the rib-shaped protruding wall 25. In the keep-closed and locked state, the relay connector 20 pushes (presses) the rear substrate 14 against the substrate support surface 22b of the housing 22 by the top plate 23a of the retaining member 23. Accordingly, it is possible to stably keep the contact between the plurality of electrodes 14c of the rear substrate 14 and the contact parts 21a of the contacts 21.

As a result, in the electronic endoscope system 50 illustrated in FIG. 1, it is possible to easily and stably secure a state in which the relay connector 20 electrically connects a display-device-side circuit including the receptacle 52 to the electric circuit of the imaging module 10 via the wiring lines 31b of the relay substrate 31 and the contacts 21.

As illustrated in FIG. 7, when no mounting object such as the rear substrate 14 of the imaging module 10 is present on the substrate support surface 22b of the housing 22, an upper end of the contact part 21a of the contact 21 is slightly positioned above the substrate support surface 22b.

Additionally, the upper end of the contact part 21a of the contact 21 is located on an extension of the substrate accommodation groove 25a between the pair of rib-shaped protruding walls 25 (width-direction positioning parts) on the housing 22.

As illustrated in FIG. 8, the rear substrate 14 of the imaging module 10 is positioned with respect to the housing 22 by the positioning pin 24 and the rib-shaped protruding wall 25, and the retaining member 23 is brought into the keep-closed and locked state. Accordingly, the contact part 21a of the contact 21 is pushed into the contact accommodation groove 26 by the rear substrate 14. In this case, the contact part 21a of the contact 21 is pushed into the contact accommodation groove 26 of the housing 22 due to the elastic deformation of the contact 21. Moreover, the elastic restoring force of the contact 21 stably maintains the contact of the rear substrate 14 with the electrode 14c.

For this reason, it is possible to stably maintain a state in which the display-device-side circuit and the electric circuit of the imaging module 10 are electrically connected to each other via the wiring lines 31b and the contacts 21 of the relay substrate 31, by the relay connector 20.

The relay connector 20 is sandwiched and fixed by pushing the rear substrate 14 of the imaging module 10 into the housing 22 by the retaining member 23 brought into the keep-closed and locked state.

The relay unit 30 is attached to the imaging module 10 by sandwiching and fixing the rear substrate 14 of the imaging module 10 with the relay connector 20.

The electronic component unit U1 is brought into an assembled state by pushing the rear substrate 14 of the imaging module 10, which is positioned with respect to the housing 22 by the positioning pin 24 and the rib-shaped protruding walls 25 of the relay connector 20, into the housing 22 using the retaining member 23 brought into the keep-closed and locked state, so as to sandwich and fix the rear substrate 14.

As illustrated in FIG. 5, a tube accommodation groove 22o capable of accommodating the tube 15 of the tube-attached module 16 is formed from the upper surface of the second pedestal part 22B to the second end surface 22f of the housing 22 on the second end surface 22f side of the housing 22 (the end part of the second pedestal part 22B of the housing 22 opposite to the contact placement region 22C).

The second end surface 22f of the housing 22 is a side surface of the second pedestal part 22B opposite to the contact placement region 22C in the longitudinal direction.

The tube accommodation groove 22o is formed such that the depth from the upper surface of the second pedestal part 22B increases toward the second end surface 22f side of the housing 22.

As illustrated in FIG. 5, the tube accommodation groove 22o is formed by being recessed from the upper surface of the second pedestal part 22B in a region corresponding to the extension of the substrate accommodation groove 25a on the upper surface of the second pedestal part 22B in the longitudinal direction.

The first end part (front end part) of the rear substrate 14 positioned on the housing 22 by the positioning pin 24 and the rib-shaped protruding walls 25 is placed on the tube accommodation groove 22o. The sub-conductor connection terminal 14d3 (refer to FIG. 10) of the rear substrate 14 is placed inside the tube accommodation groove 22o.

The portion of the tube-attached module 16 in which the tube 15 is present in the longitudinal direction is hereinafter also referred to as a tube exterior part. In the tube exterior part, an end part that accommodates the imaging element 11 is referred to as a first end part (front end part), and an end part opposite thereto is referred to as a second end part (rear end part).

The tube accommodation groove 22o accommodates the second end part (rear end part) of the tube exterior part and the rear end part of the electric cable 13 extending from the rear end of the tube 15 of the tube exterior part.

The rear substrate 14 of the tube-attached module 16 is mounted on the substrate support surface 22b of the housing 22 with such an orientation that the first main surface 14a becomes a lower surface. For this reason, the tube exterior part hangs downward from the rear substrate 14 at a portion where the substrate support surface 22b of the housing 22 is not present downward from the tube exterior part of the tube-attached module 16 in the longitudinal direction of the housing 22.

In a case where the tube accommodation groove 22o is not formed and the second end surface 22f of the housing 22 is perpendicular to the substrate support surface 22b of the housing 22, the tube-attached module 16 has a portion supported by the housing 22 and a portion in which the housing 22 is not present below the tube-attached module 16 and which is not supported by the housing 22. Since the tube-attached module 16 is locally bent in the vicinity of a boundary between the two portions, the tube 15 may be easily damaged.

As long as the tube-attached module 16 is configured to be accommodated in the tube accommodation groove 22o, it is possible to avoid a bent spot from being formed in the tube-attached module 16 that damages the tube 15. As a result, as long as the tube-attached module 16 is configured to be accommodated in the tube accommodation groove 22o, it is possible to extend the life of the tube 15 as compared to a configuration in which the tube accommodation groove 22o is not formed.

Figure 12:
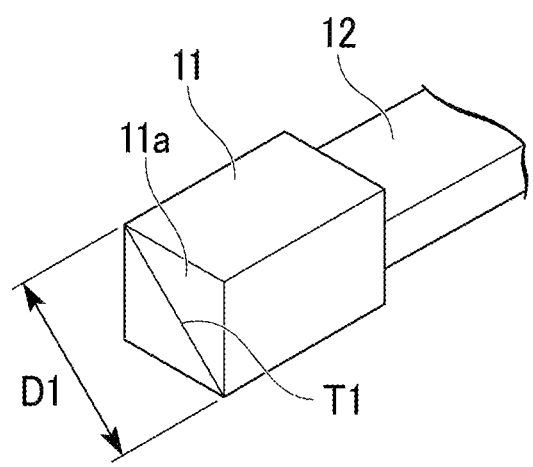
FIG. 12 is a perspective view illustrating the vicinity of an imaging element of the imaging module.

FIG. 12 illustrates a perspective view of the imaging module 10 in the vicinity of the imaging element 11. As illustrated in FIG. 12, the imaging element 11 of the imaging module 10 is a solid-state imaging element formed in an angular shape (block shape) that extends with a rectangular cross-section.

Figure 13:
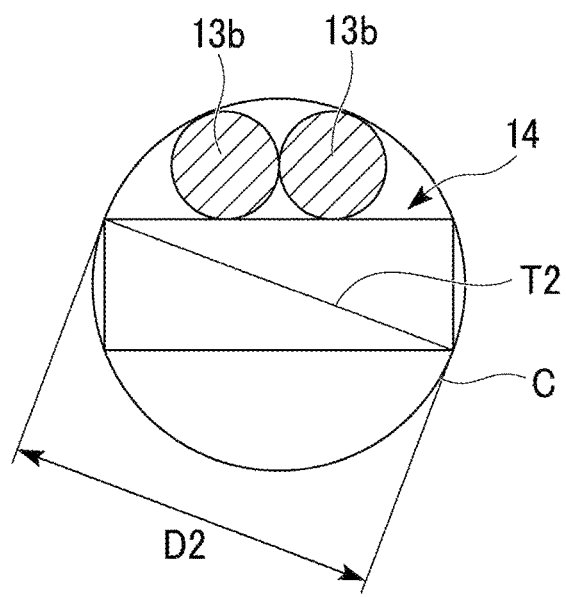
FIG. 13 is a cross-sectional view illustrating the vicinity of a front end part of the rear substrate of the imaging module.

FIG. 13 illustrates a cross-sectional view in the vicinity of the first end part (front end part) of the rear substrate of the imaging module. As illustrated in FIG. 13, the cross-sectional shape of the rear substrate 14 of the imaging module 10 extends in an oblong shape. The cross-section of the rear substrate 14 is formed in an elongated plate shape.

Here, the length of a diagonal line (first diagonal line T1) on a light receiving surface (front end surface) 11a of a front end of the imaging element 11 illustrated in FIG. 12 is set to D1, and the length of a diagonal line of the rear substrate 14 (second diagonal line T2) in a cross-section intersecting (perpendicular to) the longitudinal direction of the rear substrate 14 illustrated in FIG. 13 is set to D2.

The length D2 of the diagonal line (second diagonal line T2) in the cross-section intersecting (perpendicular to) the longitudinal direction of the rear substrate 14 of FIG. 13 is set to the length D1 or less of the diagonal line (first diagonal line T1) in the light receiving surface 11a of the front end of the imaging element 11 illustrated in FIG. 12 (that is, D1≥D2 is satisfied).

The rear substrate 14 is formed such that the length D2 of the diagonal line (second diagonal line T2) in the cross-section thereof is the length D1 or less of the diagonal line (first diagonal line T1) on the light receiving surface 11a of the front end of the imaging element 11 illustrated in FIG. 12 over the entire length in the longitudinal direction of the rear substrate 14.

Additionally, as illustrated in FIG. 13, the two coaxial cables 13b of the electric cable 13 are placed along the rear substrate 14. The two coaxial cables 13b can be placed inside a circumscribed circle C of a main body of the rear substrate 14 having the diameter of the second diagonal line T2.

In the cross-section perpendicular to the longitudinal direction of the imaging module 10, the diameter of the circumscribed circle of the head-side substrate 12 and the electric cable 13 is equal to or less than the length D1 of the first diagonal line T1. That is, the head-side substrate 12 and the electric cable 13 of the imaging module 10 are also formed such that the cross-section perpendicular to the longitudinal direction of the imaging module 10 falls within the circumference of the diameter D1 or less of the length D1 of the first diagonal line T1.

The imaging module 10 is formed such that the cross-section perpendicular to the longitudinal direction of the imaging module 10 falls within the circumference having a diameter of D1 or less of the length D1 of the first diagonal line T1 over the entire length of the imaging module 10 in the longitudinal direction.

For this reason, the tube 15 used for assembling the tube-attached module 16 only needs to have an inner diameter capable of accommodating the imaging element 11, and it is possible to reduce the diameter within a range in which the imaging element 11 is capable of accommodating.

As illustrated in FIG. 1, it is possible to assemble the electronic component unit U1 by sandwiching and fixing the rear substrate 14 of the imaging module 10 with the relay connector 20 after the assembling of the tube-attached module 16.

After the assembling of the tube-attached module 16, the electronic component unit U1 can be brought into an assembled state by simply sandwiching and fixing the rear substrate 14 of the imaging module 10 with the relay connector 20, and it is possible to realize the electrical connection between the display-device-side circuit and the electric circuit of the imaging module 10.

Second Embodiment

Figure 14:
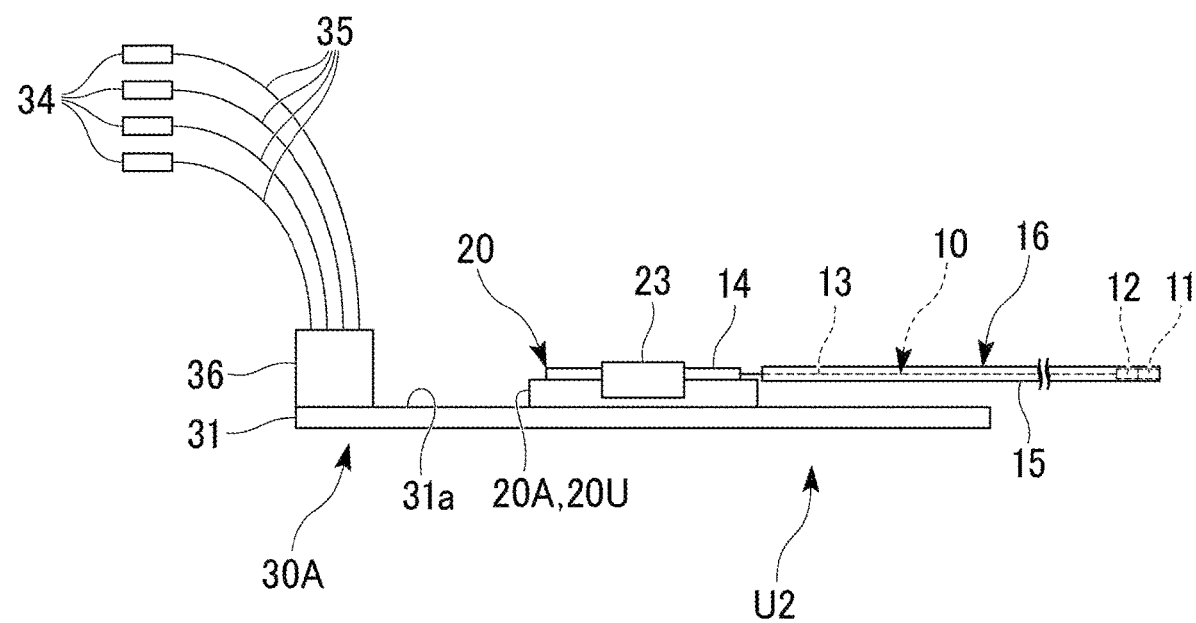
FIG. 14 is a view illustrating the vicinity of a relay unit before assembling of a substrate accommodation housing of an electronic component unit of a second embodiment.

FIG. 14 illustrates an electronic component unit U2 of a second embodiment.

As illustrated in FIG. 14, in the electronic component unit U2 of this embodiment, the relay unit in the electronic component unit U1 of the first embodiment is changed.

The imaging module 10 (electronic module) and the tube-attached module 16 are not changed. In addition, FIG. 14 illustrates an electronic component unit before the assembling of a connector housing to be described below.

In addition, in FIG. 14, the same constituent portions as those of the electronic component unit U1 of the first embodiment will be designated by common reference numerals to simplify the description thereof.

As illustrated in FIG. 14, in a relay unit 30A of the electronic component unit U2 of this embodiment, the external connection connector 32 is omitted regarding the relay unit 30 of the electronic component unit U1 of the first embodiment, and an external connection terminal 34 to which an electric wire 35 is electrically connected is adopted.

An end part (base end part) of the electric wire 35 on a side closer to the relay substrate 31 is referred to as a first end part. An end part of the electric wire 35 on a side closer to the external connection terminal 34 is referred to as a second end part. The first end part of the electric wire 35 is electrically connected to the wiring line 31b (not illustrated) of the relay substrate 31 by soldering or the like. The external connection terminal 34 may be electrically connected to the terminal connection electrode 31c of the relay substrate 31 via a connection conductor including the electric wire 35.

A tubular connection part cover 36, which covers a connection spot where the base end part of the electric wire 35 is electrically connected to the wiring line 31b of the relay substrate 31, is attached to the main surface 31a of the relay substrate 31. The electric wire 35 is electrically connected to the wiring line 31b of the relay substrate 31. The second end part (tip) of the electric wire 35 to which the external connection terminal 34 is attached extends out of the connection part cover 36 from an opening part on the connection part cover 36.

Figure 15A:
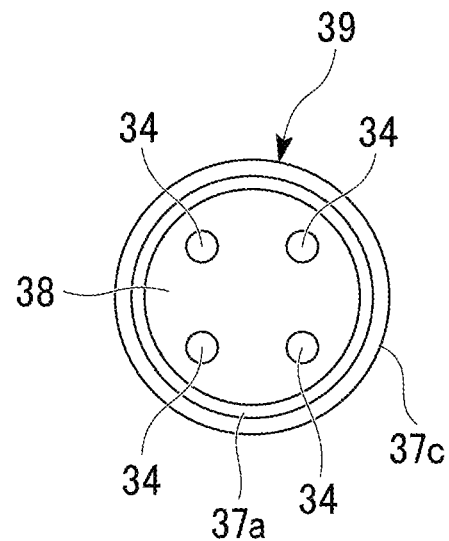
FIG. 15A is a view illustrating an example of the substrate accommodation housing assembled to the electronic component unit of FIG. 14 and an external connection connector and illustrating a structure seen from a tip (insertion end) side of the external connection connector.
Figure 15B:
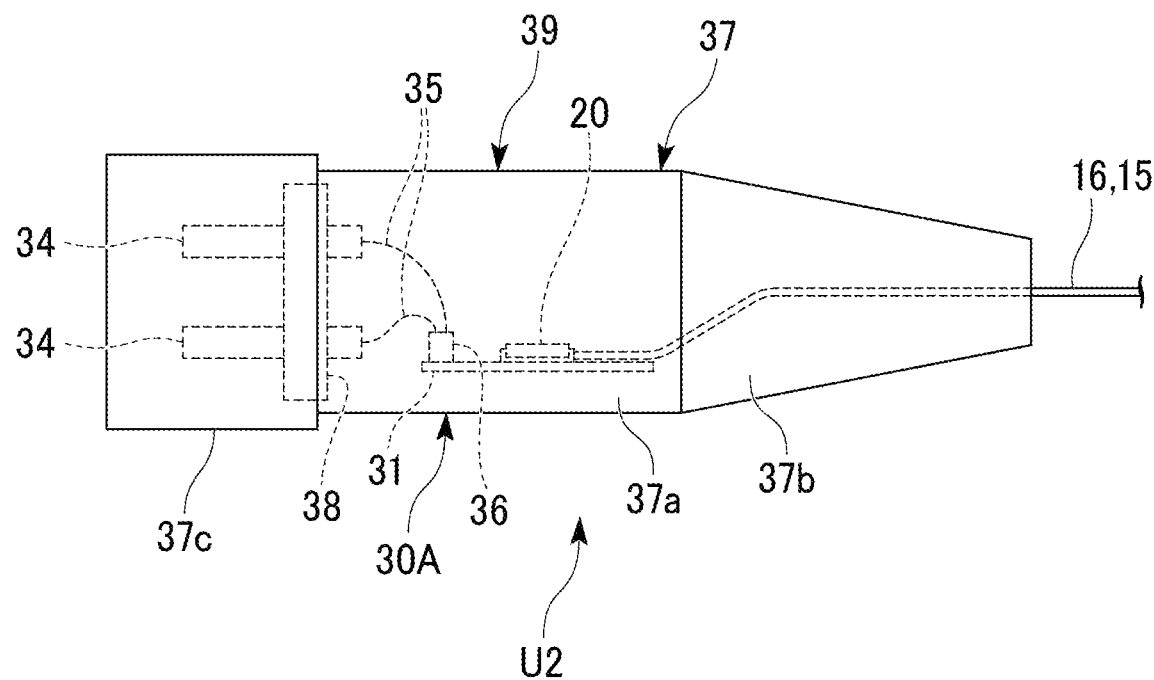
FIG. 15B is a view illustrating the example of the substrate accommodation housing assembled in the electronic component unit of FIG. 14 and the external connection connector and illustrating a structure seen from a side surface of the external connection connector.

FIGS. 15A and 15B illustrate an example of an external connection connector 39 in which a connector housing 37 is assembled around (i.e., houses) the electronic component unit U2 of FIG. 14. FIG. 15A illustrates a structure in which the external connection connector 39 is seen from the tip (insertion end) side. FIG. 15B illustrates a structure as seen from the side surface of the external connection connector 39. As illustrated in FIGS. 15A and 15B, the relay unit 30A also has the connector housing 37 that accommodates the external connection terminal 34 and is assembled around the relay substrate 31 and the relay connector 20.

The external connection terminal 34 shown as an exemplary example in FIGS. 14, 15A, and 15B is specifically a metal pin. As illustrated in FIGS. 15A and 15B, the connector housing 37 accommodates a plurality of (four in the illustrated example) the external connection terminals 34 that are metal pins. Additionally, the connector housing 37 also accommodates a terminal support plate 38 through which each external connection terminal 34 is fixed.

As illustrated in FIGS. 15A and 15B, the electronic component unit U2 of this embodiment has the external connection connector 39 having a configuration in which the plurality of external connection terminals 34, the terminal support plate 38, the relay substrate 31, and the relay connector 20 in the connector housing 37 are accommodated therein.

The connector housing 37 has a cylindrical housing body 37a, a tapered tubular boot 37b through which the tube exterior part of the tube-attached module 16 is passed, and a retaining ring 37c screwed to a front end part of the housing body 37a.

In the connector housing 37 and the housing body 37a, the side closer to the retaining ring 37c is referred to as a front end part, and the side closer to the boot 37b is referred to as a rear end part. The boot 37b is attached to a rear end part of the housing body 37a by fitting or the like. The boot 37b is formed in a tapered appearance in which the diameter decreases in a direction from the front end part side to the rear end part side of the housing body 37a.

After the tube-attached module 16 is assembled and the rear substrate 14 of the imaging module 10 is sandwiched and fixed by the relay connector 20, the work of assembling the connector housing 37 is performed. Accordingly, it is possible to assemble the connector housing 37.

Here, a method of assembling the connector housing 37 will be described.

After the assembling of the tube-attached module 16, the tube exterior part of the tube-attached module 16 is passed through the boot 37b. After that, the rear substrate 14 of the imaging module 10 is sandwiched and fixed by the relay connector 20.

After the rear substrate 14 of the imaging module 10 is sandwiched and fixed by the relay connector 20, the relay substrate 31 and the relay connector 20 are inserted into the housing body 37a from the rear end side thereof. Moreover, the terminal support plate 38 through which the external connection terminal 34 is fixed is inserted into the housing body 37a from the front end thereof.

Next, the retaining ring 37c is screwed (screwed in and attached) to the front end part of the housing body 37a. The retaining ring 37c is screwed to an outer periphery of the housing body 37a on the front end part side.

A rotational operation is performed in which the retaining ring 37c is screwed into the front end part of the housing body 37a. Accordingly, the retaining ring 37c moves toward the rear end part of the housing body 37a. Moreover, the terminal support plate 38 in the housing body 37a is pushed and fixed to the protruding wall in the housing body 37a. Additionally, a front end part of the boot 37b is attached to a rear end part of the housing body 37a.

By completing this work, the connector housing 37 and the external connection connector 39 are assembled together.

In the electronic component unit U2 having the external connection connector 39, when the external connection connector 39 is inserted and fitted into the receptacle, the electric circuit of the imaging module 10 can be simply electrically connected to the external circuit electrically connected to receptacle-side contacts.

As the external connection terminal 34, for example, it is also possible to adopt a crimp terminal attached by being crimped to the tip of the electric wire 35.

The connector housing 37 can be appropriately design-changed according to the configuration of the external connection terminal 34, and the like.

Modification Example of Relay Connector

FIGS. 16 to 19 illustrate a relay connector 220 of a modification example.

In addition, regarding the relay connector 220 of the modification example, the same constituent portion as those of the relay connector 20 of the first embodiment (hereinafter, also referred to as a relay connector of a first example) shown as an exemplary example in FIGS. 5 to 9 and the like will be designated by common reference numerals in FIGS. 16 to 19, and a description thereof will be simplified or omitted.

Additionally, the relay connector 220 of the modification example will be described with reference to FIGS. 16 to 19 with an upper side of a paper surface in the Z direction as the top and a lower side thereof as the bottom.

Figure 16:
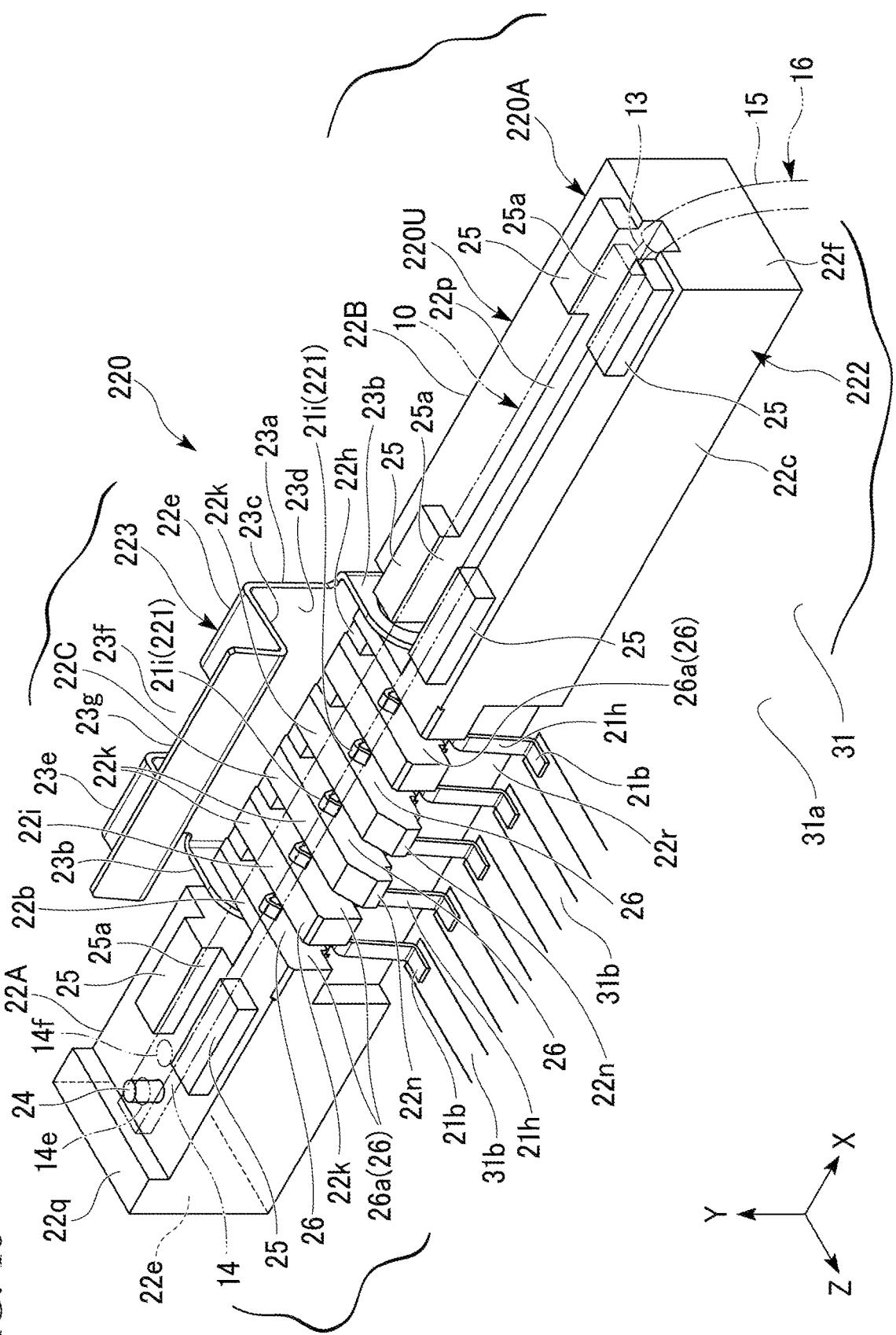
FIG. 16 is a perspective view illustrating a modification example of the relay connector and illustrating a state in which the retaining member is opened with respect to the housing.

As illustrated in FIG. 16, the relay connector 220 of the modification example has a connector base member 220A having a configuration in which an angular bar-shaped housing 222 is provided with the longitudinal positioning part 24 and the width-direction positioning part 25. Additionally, the relay connector 220 of the modification example includes a plurality of contacts 221 (relay conductors) held in the contact placement region 22C at a longitudinal central part of the housing 222, and a retaining member 223 rotatably pivoted by the housing 222.

The relay connector 220 of the modification example has a base unit 220U having a configuration in which the contacts 221 are provided on the connector base member 220A.

As illustrated in FIGS. 5 to 8, in the housing 22 of the relay connector 20 of the first example, the dimension in the front-rear direction (the spacing between the front surface 22c and the rear surface 22d) is larger the dimension in the height direction (the spacing between the bottom surface 22a and the substrate support surface 22b). That is, the housing 22 of the relay connector 20 of the first example is formed in an elongated plate shape that extends with a flat cross-section.

Figure 18:
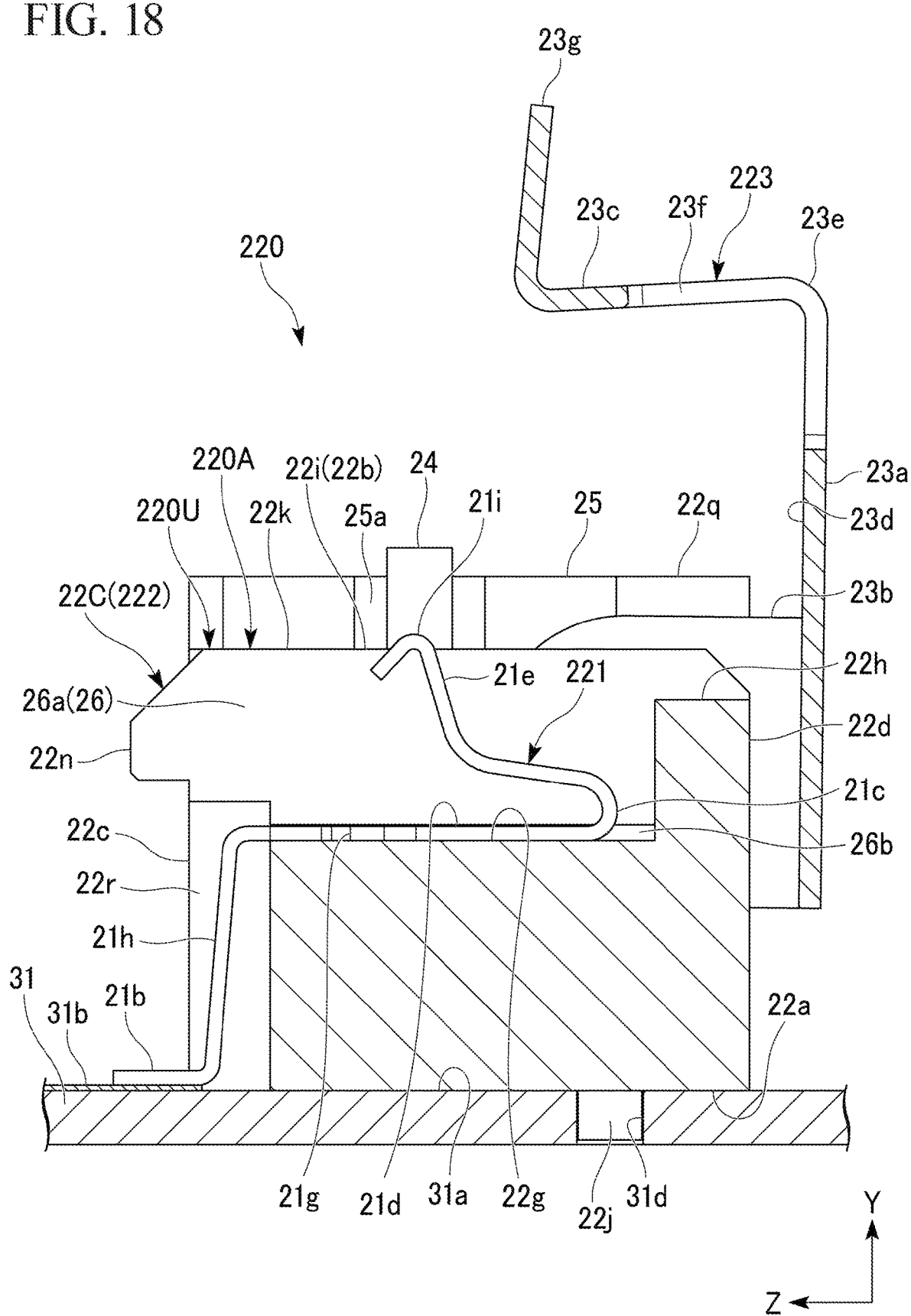
FIG. 18 is a cross-sectional view illustrating the vicinity of a contact accommodation groove of the relay connector of FIG. 16.

On the contrary, as illustrated in FIG. 18, the housing 222 of the relay connector 220 of the modification example is formed in an angular bar shape that the dimension thereof in the front-rear direction (the spacing between the front surface 22c and the rear surface 22d) is substantially the same as the dimension in the height direction (the spacing between the bottom surface 22a and the substrate support surface 22b).

As illustrated in FIG. 16, the housing 222 of the relay connector 220 of the modification example has the contact placement region 22C at the central part thereof and the pedestal parts (the first pedestal part 22A and the second pedestal part 22B) on both sides of the contact placement region 22C, in the longitudinal direction thereof.

Out of the pedestal parts on both sides of the contact placement region 22C of the housing 222, the first pedestal part 22A on one side is provided with the longitudinal positioning part 24 (the positioning pin in FIG. 16 and the like). The longitudinal positioning part 24 is not provided in the second pedestal part 22B of the housing 222 opposite to the first pedestal part 22A via the contact placement region 22C.

In addition, the dimension of the second pedestal part 22B of the housing 222 of the relay connector 220 of the modification example in the longitudinal direction of the housing 222 is larger than the dimension of the first pedestal part 22A in the longitudinal direction of the housing 222.

Regarding the first pedestal part 22A and the second pedestal part 22B, the longitudinal direction of the housing 222 is also hereinafter referred to as the longitudinal direction.

A substrate escape groove 22p extending in the longitudinal direction of the housing 222 is formed in the second pedestal part 22B of the housing 222.

The substrate escape groove 22p is formed so as to extend over the entire length of the second pedestal part 22B in the longitudinal direction of the housing 222. The substrate escape groove 22p is formed by being recessed from the substrate support surface 22b of the housing 22 in the second pedestal part 22B.

The substrate escape groove 22p is formed only in the second pedestal part 22B of the housing 222. The substrate escape groove 22p is not formed in the first pedestal part 22A and the contact placement region 22C of the housing 222.

As illustrated in FIG. 5, the connector base member 20A of the relay connector 20 of the first example has the pair of rib-shaped protruding walls 25, which form the substrate accommodation groove 25a, on each of both sides of the housing 22 in the longitudinal direction via the contact placement region 22C.

On the contrary, as illustrated in FIG. 16, the connector base member 220A of the relay connector 220 of the modification example has a configuration in which one pair of rib-shaped protruding walls 25 (width-direction positioning parts), which forms the substrate accommodation groove 25a, are provided on the first pedestal part 22A of the housing 222 and two pairs of rib-shaped protruding walls 25 are provided on the second pedestal part 22B.

In the connector base member 220A shown as an exemplary example in FIG. 16, the width direction of the substrate support surface 22b of the housing 222, which is perpendicular to the longitudinal direction coinciding with the longitudinal direction of the housing 222, coincides with the front-rear direction of the housing 222.

The rib-shaped protruding walls 25 constituting a pair forming the substrate accommodation groove 25a are provided so as to be separated from each other in the width direction of the substrate support surface 22b.

The pair of rib-shaped protruding walls 25 of the second pedestal part 22B is provided at two spots separated from each other in the longitudinal direction of the second pedestal part 22B. In the connector base member 220A shown as an exemplary example in FIG. 16 and the like, the pair of rib-shaped protruding walls 25 of the second pedestal part 22B is provided at each of both end parts of the second pedestal part 22B in the longitudinal direction.

Additionally, the pair of rib-shaped protruding walls 25 of the second pedestal part 22B is formed so as to protrude from the substrate support surfaces 22b on both sides of the substrate escape groove 22p of the second pedestal part 22B.

The rib-shaped protruding walls 25 on both sides of the substrate escape groove 22p are formed such that the entire substrate accommodation groove 25a between the rib-shaped protruding walls 25 is located on the substrate escape groove 22p.

In the connector base member 220A shown as an exemplary example in FIG. 16, inner side surfaces of the substrate escape groove 22p of the second pedestal part 22B of the housing 222 on both sides in the groove width direction are formed perpendicular to the front-rear direction of the housing 222. In the substrate accommodation groove 25a of the rib-shaped protruding walls 25 on both sides of the substrate escape groove 22p, surfaces facing each other in the groove width direction are referred to as facing surfaces of the substrate accommodation groove 25a. The facing surfaces of the substrate accommodation groove 25a are formed so as to extend perpendicularly to the front-rear direction of the housing 222 continuously from the inner side surfaces on both sides of the substrate escape groove 22p in the groove width direction.

Figure 17:
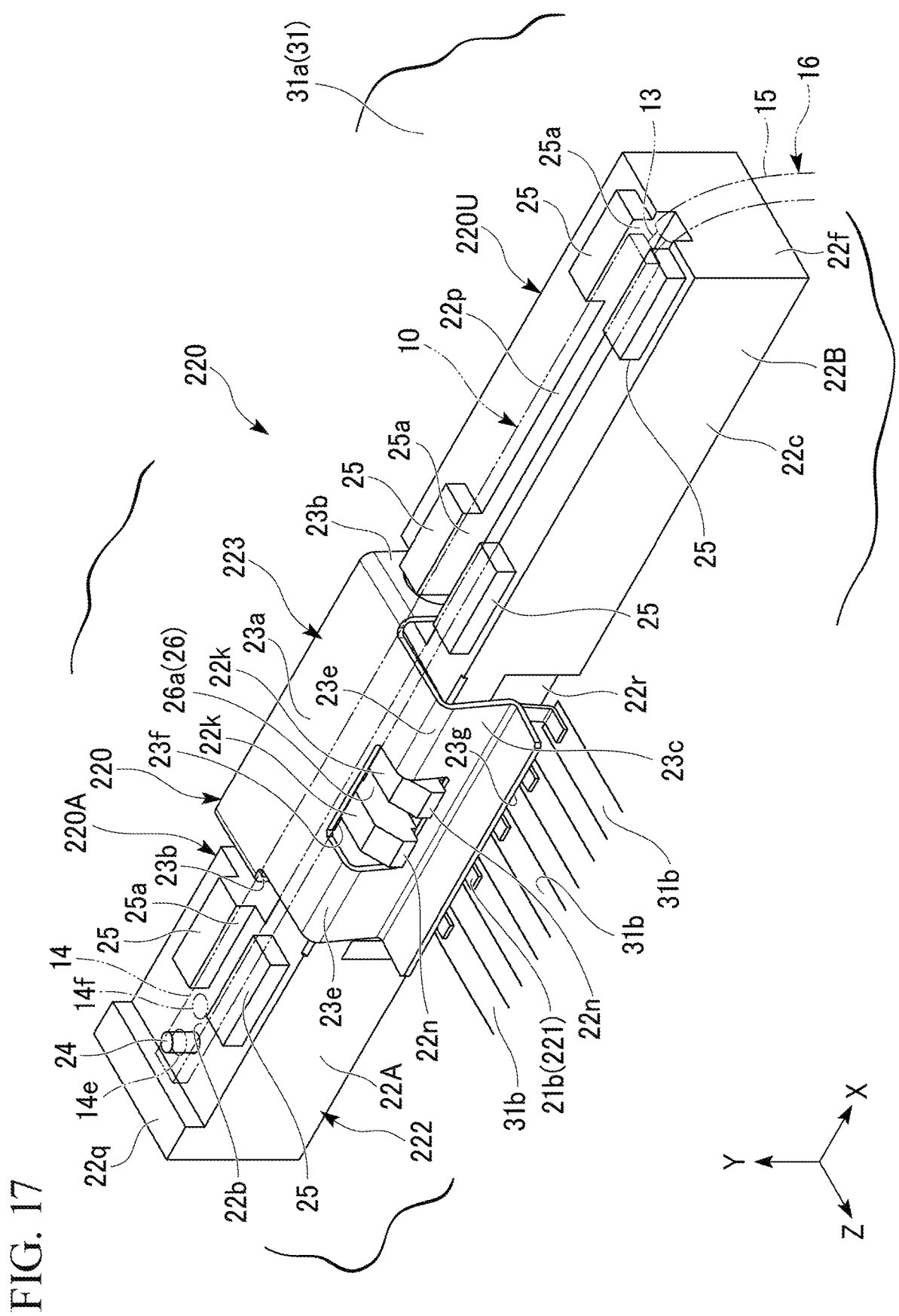
FIG. 17 a perspective view illustrating a state in which a connection end substrate (the rear substrate of the imaging module) is sandwiched between the retaining member in closed state and the housing, and brought into a keep-closed and locked state with respect to the housing, regarding the relay connector of FIG. 16.

In FIGS. 16 and 17, the rear substrate 14 of the imaging module 10 is placed on the substrate support surface 22b of the housing 222 with such an orientation that the first main surface 14a faces the substrate support surface 22b (upper surface) of the housing 222. The rear substrate 14 of the imaging module 10 is placed on the substrate support surface 22b of the housing 222 of the relay connector 220 when the retaining member 223 (pressing part) is in the open state.

The rear substrate 14 is placed on the substrate support surface 22b by being positioned in the width direction and the longitudinal direction of the substrate support surface 22b with respect to the housing 222 by the positioning pin 24 and the rib-shaped protruding walls 25 on the housing 222.

The rear substrate 14 is inserted into the substrate accommodation groove 25a secured by each of the pairs of rib-shaped protruding walls 25 at three spots of the housing 222 in the longitudinal direction. Accordingly, the rear substrate 14 is positioned in the width direction of the substrate support surface 22b (the front-rear direction of the housing 222) with respect to the housing 222.

Additionally, the positioning pin 24 on the housing 222 is inserted into the first jig hooking hole 14e of the rear substrate 14. Accordingly, the rear substrate 14 is positioned in the longitudinal direction of the substrate support surface 22b (the longitudinal direction of the housing 222) with respect to the housing 222.

As illustrated in FIG. 16, as compared to a configuration in which pairs of rib-shaped protruding walls 25 are provided at only two or one spot of the housing 222 in the longitudinal direction, a configuration in which pairs of rib-shaped protruding walls 25 are provided at three spots of the housing 222 in the longitudinal direction is advantageous in that the positioning accuracy of the rear substrate 14 in the width direction of the substrate support surface 22b with respect to the housing 222 is stably secured.

A configuration having pairs of rib-shaped protruding walls 25 at a plurality of spots of the first pedestal part 22A and the second pedestal part 22B of the housing 222 in the longitudinal direction is advantageous in that the positioning accuracy of the rear substrate 14 on the contact placement region 22C is stably secured. For example, when the electric cable 13 of the imaging module 10 is bent, shaken, or the like, it is possible to avoid affecting the positioning accuracy of the rear substrate 14 with respect to the housing 222 on the contact placement region 22C.

As illustrated in FIG. 16, the positioning pin 24 and the pair of rib-shaped protruding walls 25 are provided on the first pedestal part 22A of the housing 222 of the relay connector 220 of the modification example similarly to on the first pedestal part 22A of the housing 22 of the relay connector 20 of the first example.

Additionally, an erroneous insertion prevention protruding wall 22q is also provided on the first pedestal part 22A of the housing 222 of the relay connector 220 of the modification example. The erroneous insertion prevention protruding wall 22q is provided on the side closer to the first end surface 22e of the housing 222 and protrudes upward from the substrate support surface 22b of the housing 222. The erroneous insertion prevention protruding wall 22q prevents the positioning pin 24 on the housing 222 from being erroneously inserted into the second jig hooking hole 14f of the rear substrate 14. The connector base member 220A of the relay connector 220 of the modification example includes the erroneous insertion prevention protruding wall 22q.

Figure 19:
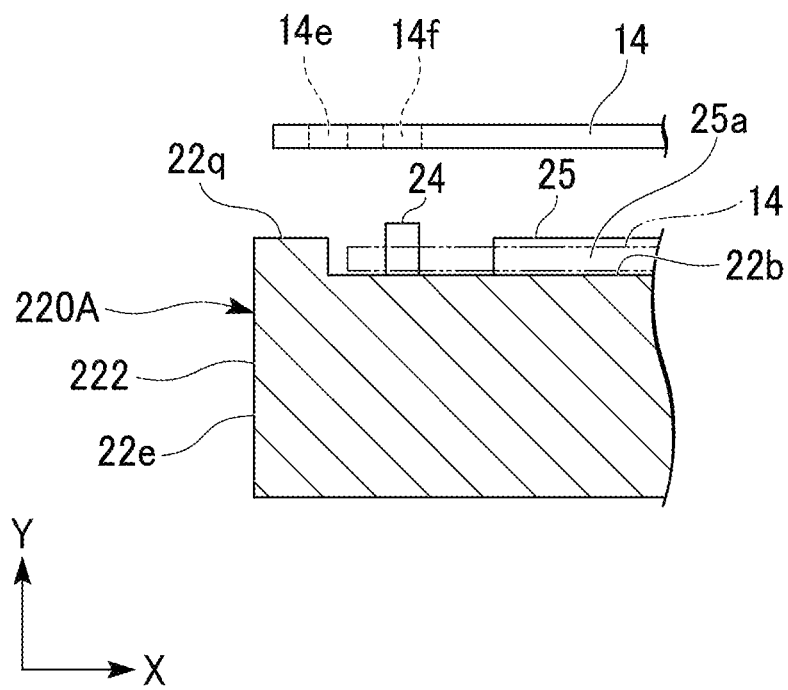
FIG. 19 is an enlarged front cross-sectional view illustrating the vicinity of a positioning pin and an erroneous insertion prevention protruding wall of the relay connector of FIG. 16.

FIG. 19 illustrates a cross-sectional view of the vicinity of the positioning pin 24 and the erroneous insertion prevention protruding wall 22q of the relay connector of FIG. 16. As illustrated in FIGS. 16 and 19, the erroneous insertion prevention protruding wall 22q is provided at a position separated from the positioning pin 24. The erroneous insertion prevention protruding wall 22q is provided on the side closer to the first end surface 22e of the housing 222 (the side opposite to the contact placement region 22C) with respect to the positioning pin 24.

The separation distance between the erroneous insertion prevention protruding wall 22q and the positioning pin 24 is larger than the dimension from a rear end of the rear substrate 14 to the first jig hooking hole 14e and is secured in a range smaller than the dimension from the rear end of the rear substrate 14 to the second jig hooking hole 14f.

As illustrated in FIG. 19, when the positioning pin 24 on the housing 222 is inserted into the first jig hooking hole 14e of the rear substrate 14, the rear substrate 14 is inserted into the substrate accommodation groove 25a between the rib-shaped protruding walls 25 of the housing 222. For this reason, it is possible to place the rear substrate 14 on the substrate support surface 22b of the housing 222. The rear substrate 14 in which the positioning pin 24 on the housing 222 is inserted into the first jig hooking hole 14e can be placed on the substrate support surface 22b of the housing 222.

The rear substrate 14 is placed on the substrate support surface 22b by inserting the positioning pin 24 on the housing 222 into the first jig hooking hole 14e. When the retaining member 223 of the relay connector 220 is closed with respect to the housing 222 from the open state, the rear substrate 14 is pressed against the housing 222 by the retaining member 223. Accordingly, the first main surface 14a of the rear substrate 14 can be brought into surface contact with the substrate support surface 22b of the housing 222. The retaining member 223 can be engaged with the locking protrusion 22n of the housing 222 to maintain the closed state of the housing 222 with respect to the contact placement region 22C.

When the positioning pin 24 on the housing 222 is to be inserted into the second jig hooking hole 14f of the rear substrate 14, a rear-end-side portion abuts onto the erroneous insertion prevention protruding wall 22q from the first jig hooking hole 14e of the rear substrate 14. That is, the rear substrate 14 is brought into a state where the rear substrate 14 rides on the erroneous insertion prevention protruding wall 22q. For this reason, the positioning pin 24 on the housing 222 cannot be inserted into the second jig hooking hole 14f of the rear substrate 14. Additionally, the first main surface 14a of the rear substrate 14 cannot be brought into surface contact with the substrate support surface 22b of the housing 222.

Additionally, when the retaining member 223 is rotated in a closing direction from the open state with respect to the housing 222 in a state in which a part of the rear substrate 14 rides on the erroneous insertion prevention protruding wall 22q, the retaining member 223 abuts against the rear substrate 14 before reaching a position where the retaining member 223 is engageable with the locking protrusion 22n of the housing 222, and cannot be engaged with the locking protrusion 22n.

For this reason, the worker who electrically connects the rear substrate 14 to the relay connector 220 (specifically, the contact 221) cannot engage the retaining member 223 with the locking protrusion 22n of the housing 222, it is possible to simply and clearly grasp that the positioning pin 24 on the housing 222 is not inserted into the first jig hooking hole 14e of the rear substrate 14.

In the relay connector 220 of the modification example, it is possible to prevent the erroneous insertion in which the positioning pin 24 on the housing 222 is inserted into the second jig hooking hole 14f of the rear substrate 14 by the erroneous insertion prevention protruding wall 22q.

Additionally, the relay connector 220 is advantageous in that a state in which the positioning pin 24 on the housing 222 is inserted into the first jig hooking hole 14e of the rear substrate 14 reliably secured.

As illustrated in FIGS. 16 to 18, a plurality (4 or more) of contact accommodation grooves 26 partitioned by groove partition walls 22k at a plurality of spots (3 or more) of the housing 222 in the longitudinal direction are formed in the contact placement region 22C of the housing 222 of the relay connector 220 of the modification example.

The locking protrusion 22n of the contact placement region 22C of the relay connector 220 of the modification example is formed, out of the groove partition walls 22k arranged at the plurality of spots of the contact placement region 22C in the longitudinal direction of the housing 222, only on the front surface 22c of the housing 22 in the groove partition wall 22k located between the groove partition walls 22k at both ends of the arrangement. No locking protrusions 22n are formed on the front surface 22c of the housing in the groove partition walls 22k at both ends in the longitudinal direction.

In FIG. 16, the locking protrusions 22n are formed on the front surface 22c of the housing in the two groove partition walls 22k of the contact placement region 22C.

In addition, the number of groove partition walls 22k on which the locking protrusions 22n are formed is not limited to two and may be one or three or more.

The number of groove partition walls 22k in which no locking protrusions 22n are formed may be two or more including the groove partition walls 22k located on both sides of the groove partition wall 22k in which the locking protrusion 22n is formed in the longitudinal direction of the housing 222, or may be 3 or more.

The locking protrusions 22n of the relay connector 220 of the modification example are formed so as to protrude toward the front side (the side opposite to the rear surface 22d) of the housing 222 from the groove partition walls 22k at both ends of the housing 222 in the longitudinal direction.

As illustrated in FIG. 17, the retaining member 223 can engage the engaging plate piece 23c placed below the locking protrusion 22n with the locking protrusion 22n by accommodating the locking protrusion 22n of the housing 222 in the engaging window hole 23f. As a result, the retaining member 223 is restricted from rotating in an opening direction thereof by the locking protrusion 22n, and the closed state thereof with respect to the contact placement region 22C is maintained. The locking protrusion 22n locks the retaining member 223. In this way, the locking protrusion 22n can restrict the rotation of the retaining member 223 in the opening direction.

Compared to the retaining member 23 of the relay connector 20 of the first example, the retaining member 223 of the relay connector 220 of the modification example has a smaller number of locking protrusions 22n inserted into the engaging window hole 23f. For this reason, compared to the retaining member 23 of the relay connector 20 of the first example, the retaining member 223 of the relay connector 220 of the modification example has a configuration in which the size of the engaging window hole 23f in the direction (extending direction) along the longitudinal direction of the housing 22 is reduced and the size of the continuous part 23e is enlarged. The configuration of the retaining member 223 of the relay connector 220 of the modification example other than the sizes of the engaging window hole 23f and the continuous part 23e is the same as that of the retaining member 23 of the relay connector 20 of the first example.

Since the retaining member 223 of the relay connector 220 of the modification example can secure a large size of the continuous part 23e in the longitudinal direction (extending direction) of the housing 222, it is possible to enhance the durability of the continuous part 23e, compared to the retaining member 23 of the relay connector 20 of the first example.

As illustrated in FIG. 18, the relay connector 220 of the modification example adopts the contact 221 in which the contact 21 of the relay connector 20 of the first example is slightly redesigned.

Compared to the relay connector 20 of the first example, the contact part 21a, which is a rib-shaped protrusion formed to extend in the extending direction of the movable plate part 21e on the external angle side of the tip bent part 21i of the movable plate part 21e, is omitted from the contact 221 illustrated in FIG. 18. In the contact 221, the tip bent part 21i itself of the movable plate part 21e serves as the contact part.

In the extending direction of the main plate part 21d, the central bent part 21c is placed on the side closer to one end part of the main plate part 21d, and the extending part 21h is placed on the side closer to the other end part. Additionally, the extending part 21h of the contact 221 shown as an exemplary example in FIG. 18 is formed so as to extend substantially perpendicular to the main plate part 21d toward the side opposite to the side where the movable plate part 21e is bent. In the extending direction of the extending part 21h, the main plate part 21d is placed on one end part of the extending part 21h, and the connection part 21b of the contact 221 is placed on the other end part. The connection part 21b of the contact 221 extends parallel to the main plate part 21d toward the side opposite to the side where the main plate part 21d is bent through the plate thickness of the extending part 21h.

As illustrated in FIGS. 16 to 18, an extending part placement recess 22r in which a lower side of each groove partition wall 22k is recessed from the front surface 22c of the housing 222 is formed on the front surface of the contact placement region 22C of the housing 222.

The extending part 21h of the contact 221 is placed in the extending part placement recess 22r of the housing 222.

As illustrated in FIG. 16, a front end (an end opposite to the rear surface 22d of the housing 222) of the groove partition wall 22k on which no locking protrusion 22n is formed constitutes a part of the front surface 22c of the housing 222.

The retaining member 223 in the open state is rotatable in the closing direction to a position where the engaging plate piece 23c abuts against the front end of the groove partition wall 22k in which no locking protrusion 22n is formed. As the engaging plate piece 23c of the retaining member 223 abuts against the front end of the groove partition wall 22k in which no locking protrusion 22n is formed, further rotation thereof in the closing direction is restricted. For this reason, even in a case where the retaining member 223 is brought into the closed state with respect to the contact placement region 22C of the relay connector 220, the retaining member 223 does not come into contact with the extending part 21h of the contact 221. Accordingly, it is possible to prevent the extending part 21h from being damaged by the contact between the retaining member 223 and the extending part 21h.

As illustrated in FIGS. 16 and 17, the rear substrate 14 of the imaging module 10 is positioned with respect to the housing 222 by the positioning pin 24 and the rib-shaped protruding walls 25 on the housing 222 and is placed on the substrate support surface 22b of the housing 222 with such an orientation that the first main surface 14a faces the substrate support surface 22b (upper surface) of the housing 222. Next, the rear substrate 14 keeps the closed state with respect to the housing 222 by engaging (locking) the retaining member 223 rotated in the closing direction with respect to the housing 222 from the open state with the locking protrusion 22n of the housing 222. Accordingly, the rear substrate 14 is pressed against the support surface 22i on the placement region of the contact placement region 22C by the top plate 23a of the retaining member 223 and is fixed to the housing 222.

As illustrated in FIG. 18, the tip bent part 21i of the contact 221 protrudes slightly upward from the support surface 22i on the placement region of the contact placement region 22C in a state before the rear substrate 14 is mounted on the upper side thereof.

When the retaining member 223 in the open state is rotated in the closing direction, the rear substrate 14 placed on the housing 222 pushes the movable plate part 21e of the contact 221 into the contact accommodation groove 26 of the housing 22. In the closed state, the rear substrate 14 is pressed against the substrate support surface 22b of the housing 222.

As a result, when the rear substrate 14 is pressed and fixed to the substrate support surface 22b of the housing 222 by the retaining member 223, the tip bent part 21i of the contact 221 stably maintains the contact with the electrode 14c of the rear substrate 14 due to the elastic restoring force of the contact 221.

The rear substrate 14 pressed and fixed to the substrate support surface 22b of the housing 222 by the retaining member 223 is supported parallel to the substrate support surface 22b by the substrate support surface 22b.

However, the portion of the rear substrate 14 located on the second pedestal part 22B of the housing 222 is placed on the substrate escape groove 22p formed in the second pedestal part 22B.

One end of the substrate escape groove 22p in the extending direction is open to the second end surface 22f of the housing 222. The substrate escape groove 22p is formed so as to extend over almost the entire length of the second pedestal part 22B in the longitudinal direction from the second end surface 22f of the housing 222 to the vicinity of the contact placement region 22C.

The rear substrate 14 is pressed against the substrate support surface 22b located in the first pedestal part 22A and the contact placement region 22C of the housing 222 by the retaining member 223. Accordingly, the rear substrate 14 is supported by the substrate support surface 22b. The portion of the rear substrate 14 located on the second pedestal part 22B bends to be located lower as the separation distance from the support surface 22i on the placement region to the second pedestal part 22B increases. The rear substrate 14 is brought in a state where at least a part thereof is accommodated in the substrate escape groove 22p or a state in which the rear substrate 14 overhangs from the support surface 22i on the placement region onto the substrate escape groove 22p.

In the relay connector 220 of the modification example, a connection spot where the conductor of the electric cable 13 is electrically connected to the conductor connection terminal 14d at the front end part of the first main surface 14a of the rear substrate 14 by soldering or the like can be accommodated in the substrate escape groove 22p to the second pedestal part 22B. Additionally, the portion of the electric cable 13 placed along the front end part of the first main surface 14a of the rear substrate 14 and an end part of the flexible tube 15 accommodating the electric cable 13 can also be accommodated in the substrate escape groove 22p.

As a result, it is possible to avoid a connection spot where the conductor of the electric cable 13 is electrically connected to the conductor connection terminal 14d at the front end part of the first main surface 14a of the rear substrate 14 by soldering or the like, a portion of the electric cable 13 placed along the front end part of the first main surface 14a of the rear substrate 14, and the tube 15, from affecting the abutment state of the rear substrate 14 against the substrate support surface 22b of the housing 222.

In the relay connector 220 of the modification example, even when the connection spot where the conductor of the electric cable 13 is electrically connected to the front end part of the first main surface 14a of the rear substrate 14 is present, it is possible to prevent the rear substrate 14 from floating with respect to the support surface 22i on the placement region (the rear substrate 14 from being separated from the support surface 22i on the placement region) of the contact placement region 22C. For this reason, the abutment state of the rear substrate 14 with respect to the support surface 22i on the placement region can be stably and reliably maintained.

Additionally, in the relay connector 220 of the modification example, even when the electric cable 13 and the end part of the tube accommodating the electric cable 13 are placed along the front end part of the first main surface 14a of the rear substrate 14, It is possible to prevent the rear substrate 14 from being separated from the support surface 22i on the placement region of the contact placement region 22C. For this reason, the abutment state of the rear substrate 14 with respect to the support surface 22i on the placement region can be stably and reliably maintained.

As a result, the relay connector 220 can stably maintain the connection state between the contact part of the contact 221 (the tip bent part 21i in FIG. 16) and the electrode 14c of the rear substrate 14, and the electrical connection state between the circuit of the imaging module 10 and the contact 221 can be kept stable.

As exemplified by the modification example, (1) providing the pair of rib-shaped protruding walls 25 (width-direction positioning parts) forming the substrate accommodation groove 25a at the plurality of spots of the second pedestal part 22B in the longitudinal direction, (2) forming the substrate escape groove 22p in the second pedestal part 22B of the housing, and (3) providing a configuration in which the rib-shaped protruding walls 25 are provided in the second pedestal part 22B to constitutes a pair forming the substrate accommodation groove 25a and the pair of rib-shaped protruding walls 25 are provided on both sides of the substrate accommodation groove 25a in the groove width direction, can be widely applied to the relay connectors of various embodiments according to the present invention, such as the relay connector of the first example.

Additionally, (4) providing the erroneous insertion prevention protruding wall 22q in the vicinity of the positioning pin 24 of the first pedestal part 22A, and (5) using the tip bent part 21i of the contact as the contact part, can be widely applied to the relay connectors of various embodiments according to the present invention, such as the relay connector of the first example.

Additionally, as illustrated in the modification example, (6) providing the locking protrusions 22n only in some of the plurality of groove partition walls 22k of the contact placement region 22C, and (7) both ends of the engaging plate piece 23c of the retaining member (both sides via the engaging window hole 23f) being capable of abutting against the front end of the groove partition wall 22k in which no locking protrusion 22n is not provided, in the longitudinal direction of the housing, can be widely applied to the relay connectors of various embodiments according to the present invention, such as the relay connector of the first example.

As in the relay connector of the first example, (8) the contact part 21a of the contact being the rib-shaped protrusion formed to extend in the extending direction of the movable plate part 21e on the external angle side of the tip bent part 21i of the movable plate part 21e, (9) providing one pair of rib-shaped protruding walls 25 forming the substrate accommodation groove 25a in each of the first pedestal part 22A and the second pedestal part 22B of the housing, (10) providing the locking protrusions 22n on all of the plurality of groove partition walls 22k of the contact placement region 22C, and (11) adopting a retaining member in which the engaging window hole 23f capable of accommodating the locking protrusions 22n provided on all of the plurality of groove partition walls 22k of the contact placement region 22C are formed, can be widely applied to the relay connectors of various embodiments according to the present invention, such as the relay connector of the modification example.

Additionally, as in the relay connector of the first example, (12) adopting a housing in which no substrate escape groove 22p is formed, and (13) adopting a housing in which no erroneous insertion prevention protruding wall 22q is provided, can be widely applied to the relay connectors of various embodiments according to the present invention, such as the relay connector of the modification example.

The tube accommodation groove 22o (refer to FIG. 5) exemplified by the relay connector of the first example can also be applied to the second pedestal part 22B in which the substrate escape groove is formed, for example, as in the housing of the relay connector of the modification example.

However, the tube accommodation groove applied to the second pedestal part 22B in which the substrate escape groove is formed is formed from the substrate escape groove (specifically, the groove bottom thereof) toward the second end surface 22f of the second pedestal part 22B opposite to the contact placement region 22C. The tube accommodation groove is formed such that the depth from the upper surface of the second pedestal part 22B increases toward the second end surface 22f side.

The cross-sectional shape of the housing can be appropriately changed.

In this respect, for example, the housing of the relay connector of the first example may be changed to an angular bar shape in which the dimension of the housing in the front-rear direction, which is the spacing direction between the front surface 22c and the rear surface 22d, is substantially the same as the dimension thereof in the height direction. Additionally, the housing of the relay connector of the modification example may be changed to an elongated plate shape that extends with a flat cross-section in which the dimension thereof in the front-rear direction, which is the spacing direction between the front surface 22c and the rear surface 22d, is larger than the dimension thereof in the height direction.

Although the present invention has been described above on the basis of the best modes, the present invention is not limited to the above-described best modes, and various modifications can be made without departing from the spirit of the present invention.

In the above-described embodiments, as an example of the electronic module, the imaging module in which the imaging element is used as the electronic element is an exemplary example. However, the electronic module is not limited to the imaging module.

In the electronic module, for example, a configuration in which a laser element or a sensor element that outputs laser light is used instead of the imaging element can also be adopted for the electronic elements of the imaging modules of the above-described embodiments.

The retaining member that presses the rear substrate of the electronic module against the contact part of the contact provided in the housing is not limited to the retaining member pivoted by the housing.

As the retaining member, for example, a clip-shaped elastic member, which sandwiches the rear substrate together with the housing in the up-down direction and presses the rear substrate against the contact part of the contact, can also be adopted.

The clip-shaped elastic member has an engaging part that is placed to abut against the bottom surface of the housing and a retaining part that presses the rear substrate from the side opposite to the housing toward the housing (specifically, the substrate support surface of the housing) and adopts a configuration in which the rear substrate is capable of being sandwiched together with the housing between the engaging part and the retaining part.

The relay conductor is not limited to the contact 21 that is formed of the metal strip and elastically deformable by the pressing of the rear substrate.

The relay conductor may be electrically connected to the wiring line of the relay substrate and may be provided so as to be capable of being electrically connected by contacting the electrode of the rear substrate in the connector base member and may be, for example, a wiring line formed on the connector base member, including the contact part that is an electrode pad on the substrate support surface of the connector base member.

The width-direction positioning part positions the rear substrate with respect to the housing in the direction perpendicular to the positioning direction of the longitudinal positioning part on the substrate support surface of the housing.

In a case where the rear substrate is an elongated plate-shaped substrate in which one surface thereof is placed so as to abut against the substrate support surface of the housing, the width-direction positioning parts align in the longitudinal direction of the rear substrate on the substrate support surface with the arrangement direction (arrangement pitch direction) of the plurality of contacts in the housing and positions the rear substrate at a predetermined position in the width direction. (Here, the width direction is the direction perpendicular to the contact arrangement direction (arrangement pitch direction) of the rear substrate on the substrate support surface). Additionally, in this case, the longitudinal positioning part positions the rear substrate positioned by the width-direction positioning part at a predetermined position in the contact arrangement direction (arrangement pitch direction) with respect to the housing.

As the longitudinal positioning part and the width-direction positioning part are, for example, a positioning protrusion formed to protrude on the housing so as to surround the periphery of the placement position of the rear substrate set on the substrate support surface of the housing, a positioning groove which is recessed from the housing and has a configuration in which a bottom surface thereof serves as the substrate support surface, and the like can also be adopted.

The protruding part that protrudes onto the substrate support surface of the housing to constitute the width-direction positioning part is not limited to the rib-shaped protruding wall described in the above-described embodiments. The shape of the protruding part that constitutes the width-direction positioning part can be appropriately changed.

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

REFERENCE SIGNS LIST

10 Electronic module (imaging module)
11 Imaging element
11a Light receiving surface (front end surface)
12 Head-side substrate
13 Electric cable
13a Exterior covering
13b Coaxial cable
13c Central conductor
13d External conductor
14 Rear substrate
14a First main surface
14b Second main surface
14c Electrode
14d Conductor connection terminal
14d1 Central conductor connection terminal
14d2 External conductor connection terminal
14d3 Sub-conductor connection terminal
14e Pin locking hole (first jig hooking hole)
14f Pin locking hole (second jig hooking hole)
15 Tube
16 Tube-attached module
20 Relay connector
20A Connector base member
20U Base unit
21 Relay conductor, contact
21a Contact part
21b Connection part
21c Central bent part
21d Main plate part
21e Movable plate part
21f Overhanging part
21g Fixing projection
21h Extending part
21i Tip bent part
22 Housing
22A First pedestal part
22B Second pedestal part
22C Contact placement region
22a Bottom surface
22b Substrate support surface
22c Front surface
22d Rear surface
22e First end surface
22f Second end surface
22g Groove bottom wall 22h Groove rear wall
22i Support surface on placement region
22j Fitting projection
22k Groove partition wall
22m Locking groove
22n Locking protrusion (locking part)
22o Tube accommodation groove
22p Substrate escape groove
22q Erroneous insertion prevention protruding wall
22r Extending part placement recess
23 Retaining member
23a Retaining part (top plate)
23b Pivoting protruding piece
23c Engaging part (engaging plate piece)
23d Retaining surface
23e Continuous part
23f Engaging window hole
23g Operating piece
24 Longitudinal positioning part, positioning pin
24a Positioning pin (second positioning pin)
25 Width-direction positioning part, protruding part (rib-shaped protruding wall)
25a Substrate accommodation groove
26 Contact accommodation groove
26a Main groove part
26b Guide groove
27 Rotary shaft
30, 30A Relay unit
31 Relay substrate
31a Main surface
31b Wiring line
31c Terminal connection electrode
32 External connection connector
32a External connection terminal
32b Terminal support
32c Accommodation tube
32d Mating contact insertion space
33 Substrate accommodation housing
34 External connection terminal
35 Electric wire
36 Connection part cover
37 Connector housing
37a Housing body
37b Boot
37c Retaining ring
38 Terminal support plate
39 External connection connector
220 Relay connector
221 Relay conductor, contact
220A Connector base member
220U Base unit
222 Housing
223 Retaining member
50 Electronic endoscope system
51 Video processing display device
52 Receptacle
U1, U2 Electronic component unit (imaging unit)

What is claimed is:

1. An electronic component unit comprising:
an electronic module in which a rear substrate is electrically connected via an electric cable to an electronic element, wherein the electronic element is any one of:
an imaging element;
a laser element; and
a sensor element;
an external connection terminal that is electrically connected to an external circuit;
a relay substrate comprising a terminal connection electrode to which the external connection terminal is electrically connected either directly or via a connection conductor; and
a relay connector on the relay substrate,
wherein
the relay connector comprises:
a connector base member attached to the relay substrate;
a relay conductor on the connector base member and that is electrically connected to the terminal connection electrode via a wiring line on the relay substrate; and
a retaining member that sandwiches the rear substrate of the electronic module between the retaining member and the connector base member and that presses an electrode on the rear substrate against a contact of the relay conductor, and
the relay connector causes the electrode on the rear substrate to contact the relay conductor such that the electrode on the rear substrate is electrically connected to the relay conductor.

2. The electronic component unit according to claim 1, further comprising:
an external connection connector attached to the relay substrate, wherein
the external connection connector comprises:
a terminal support comprising the external connection terminal; and
an accommodation tube that:
is attached to the relay substrate,
protrudes from an outer periphery of the relay substrate, and
accommodates the terminal support,
the external connection terminal is disposed on a surface of the terminal support
facing a mating contact insertion space secured in the accommodation tube, and
a base end part of the external connection terminal adjacent to the relay substrate is electrically connected to the terminal connection electrode.

3. The electronic component unit according to claim 1, further comprising:
a connector housing that accommodates the external connection terminal and that houses the relay substrate and the relay connector, wherein
the external connection terminal is electrically connected to the terminal connection electrode via the connection conductor, and
the connection conductor comprises an electric wire that is electrically connected to the external connection terminal.

4. The electronic component unit according to claim 1, wherein
the connector base member has a substrate support surface against which the rear substrate abuts, and
the retaining member comprises:
an engaging part that engages with the connector base member; and
a retaining part that pushes the rear substrate onto the substrate support surface when the engaging part is engaged with the connector base member.

5. The electronic component unit according to claim 1, wherein $D1 \geq D2$ is satisfied, where $D1$ is a length of a first diagonal line on a front end surface of the electronic element of the electronic module and $D2$ is a length of a second diagonal line of the rear substrate in a cross-section perpendicular to a longitudinal direction of the rear substrate.

\* \* \* \* \*